United States Patent
Warner

(10) Patent No.: US 7,422,432 B2
(45) Date of Patent: *Sep. 9, 2008

(54) SYSTEM AND METHOD FOR REMOTELY CONTROLLING DEVICES

(75) Inventor: Thomas P. Warner, Rochester Hills, MI (US)

(73) Assignee: Warner Systems, LLC, Rochester Hills, MI (US)

( * ) Notice: Subject to any disclaimer, the term of this patent is extended or adjusted under 35 U.S.C. 154(b) by 636 days.

This patent is subject to a terminal disclaimer.

(21) Appl. No.: 10/730,678

(22) Filed: Dec. 8, 2003

(65) Prior Publication Data

US 2004/0115591 A1 Jun. 17, 2004

Related U.S. Application Data

(63) Continuation-in-part of application No. 10/464,369, filed on Jun. 17, 2003.

(60) Provisional application No. 60/389,229, filed on Jun. 17, 2002.

(51) Int. Cl.
*A61C 1/02* (2006.01)
*H01H 3/14* (2006.01)

(52) U.S. Cl. .................. 433/101; 433/98; 200/86.5

(58) Field of Classification Search ............... 433/101, 433/98, 99; 606/34; 200/86.5
See application file for complete search history.

(56) References Cited

U.S. PATENT DOCUMENTS

| | | | |
|---|---|---|---|
| 3,742,167 A | 6/1973 | Muther | 200/86.5 |
| 3,809,454 A | 5/1974 | Brambring | 350/84 |
| 3,980,848 A | 9/1976 | Schulz et al. | 200/86.5 |
| 3,980,849 A | 9/1976 | Straihammer | 200/86.5 |
| 3,983,344 A | 9/1976 | Straihammer | 200/86.5 |
| 4,041,609 A | 8/1977 | Bresnahan et al. | 32/22 |
| 4,114,275 A * | 9/1978 | Jones et al. | 433/101 |
| 4,156,187 A * | 5/1979 | Murry et al. | 324/142 |
| 4,171,572 A * | 10/1979 | Nash | 433/29 |
| 4,180,812 A * | 12/1979 | Kaltenbach et al. | 433/28 |
| 4,305,126 A * | 12/1981 | Beier et al. | 433/28 |
| 4,354,838 A | 10/1982 | Hoyer et al. | 433/101 |
| 4,383,167 A | 5/1983 | Gmeinder et al. | 377/2 |
| 4,417,875 A | 11/1983 | Matsui | 433/101 |
| 4,523,911 A | 6/1985 | Braetsch et al. | 433/101 |
| 4,571,681 A * | 2/1986 | Beier et al. | 433/181 |
| 4,798,535 A | 1/1989 | Nielsen | 433/101 |
| 4,837,857 A | 6/1989 | Scheller et al. | 455/617 |
| 4,983,901 A | 1/1991 | Lehmer | 318/685 |
| 5,249,121 A | 9/1993 | Baum et al. | 364/413.01 |
| 5,355,804 A * | 10/1994 | Garcia et al. | 104/93 |

(Continued)

OTHER PUBLICATIONS

*Wireless Digital Footswitch*, Dental Products Report, Sep. 2003.
*Wireless Wonders: Bear Foot Pedal's Foot Control*, Dental Products Report, Dec. 2001.
Schleyer, Titus K.L., D.M.D., Ph.D, et al., *The Technologically Well-Equipped Dental Office*, The Journal of the American Dental Association, vol. 134, Jan. 2003, pp. 30-41.

*Primary Examiner*—John J Wilson

(57) ABSTRACT

A system and a method for remotely controlling devices are provided. The system includes a foot pedal unit having a moveable member. The system further includes a transmitter operatively associated with the moveable member. The transmitter transmits a first signal in response to at least partial displacement of the moveable member when a first device is selected. The transmitter transmits a second signal in response to at least partial displacement of the moveable member when a second device is selected.

24 Claims, 14 Drawing Sheets

U.S. PATENT DOCUMENTS

| | | | |
|---|---|---|---|
| 5,408,284 A * | 4/1995 | Berger et al. | 353/103 |
| 5,422,521 A | 6/1995 | Neer et al. | 307/119 |
| 5,423,231 A | 6/1995 | Helfrich et al. | 74/561 |
| 5,554,894 A | 9/1996 | Sepielli | 307/119 |
| 5,580,347 A | 12/1996 | Reimels | 604/30 |
| 5,635,777 A | 6/1997 | Telymonde et al. | 307/119 |
| 5,712,460 A | 1/1998 | Carr et al. | 200/86.5 |
| 5,883,615 A | 3/1999 | Fago et al. | 345/156 |
| 5,931,669 A * | 8/1999 | Fornoff et al. | 433/28 |
| 6,074,388 A * | 6/2000 | Tockweiler et al. | 606/34 |
| 6,179,829 B1 | 1/2001 | Bisch et al. | 606/1 |
| 2003/0004497 A1 | 1/2003 | Chappuis | 606/1 |

* cited by examiner

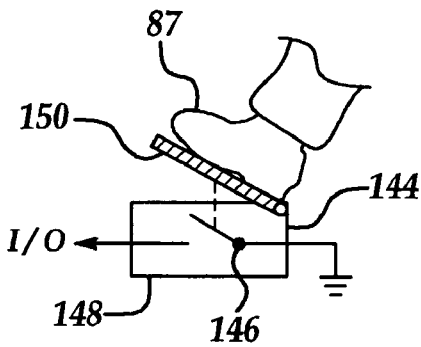
Figure 5

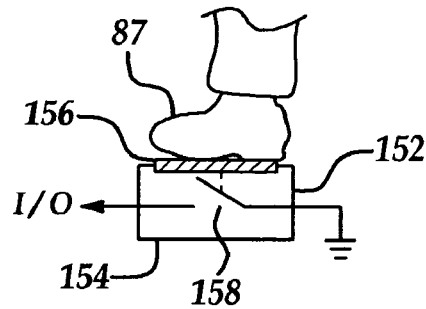
Figure 6

TRAINING MODE MESSAGE TRANSMITTED FROM HAND-HELD UNIT TO DEVICE ACTUATION UNIT

| HAND-HELD ID | MESSAGE LENGTH (# OF BYTES) | DEVICE ACTUATION UNIT ID | TRAINING MODE CODE | CHECKSUM |
|---|---|---|---|---|
| 11111111 | 00000101 | 00000001 | 11110000 | 11110001 |

Figure 7A — 170

ACKNOWLEDGEMENT MESSAGE TRANMITTED FROM DEVICE ACTUATION UNIT
TO HAND-HELD UNIT AFTER DEVICE ACTUATION UNIT RECEIVES TRAINING MODE MESSAGE

| HAND-HELD ID | MESSAGE LENGTH | DEVICE ACTUATION UNIT ID | DEVICE ACTUATION UNIT ID | CHECKSUM |
|---|---|---|---|---|
| 11111111 | 00000101 | 00000001 | 00000001 | 00000010 |

Figure 7B — 172

DEVICE SELECTION MESSAGE TRANSMITTED FROM HAND-HELD UNIT TO
FOOT-PEDAL CONTROL SYSTEM TO SELECT DEVICE

| HAND-HELD ID | MESSAGE LENGTH | DEVICE ACTUATION UNIT ID | CHECKSUM |
|---|---|---|---|
| 11111111 | 00000100 | 00000001 | 00000001 |

Figure 8A — 174

ACKNOWLEDGEMENT MESSAGE TRANSMITTED FROM FOOT PEDAL CONTROL SYSTEM TO HAND-HELD
UNIT AFTER FOOT-PEDAL CONTROL SYSTEM RECEIVES DEVICE SELECTION MESSAGE

| HAND-HELD ID | MESSAGE LENGTH | DEVICE ACTUATION UNIT ID | DEVICE ACTUATION UNIT ID | CHECKSUM |
|---|---|---|---|---|
| 11111111 | 00000100 | 00000001 | 00000001 | 00000010 |

*Figure 8B*  176

DEVICE ACTUATION MESSAGE TRANSMITTED FROM FOOT PEDAL CONTROL SYSTEM
TO DEVICE ACTUATION UNIT FOR "ON-OFF" CONTROL OF A DEVICE

| HAND-HELD ID | MESSAGE LENGTH | DEVICE ACTUATION UNIT ID | ACTUATION CODE | CHECKSUM |
|---|---|---|---|---|
| 11111111 | 00000101 | 00000001 | 01010000 | 01010001 |

*Figure 9*  178

DEVICE ACTUATION MESSAGE TRANSMITTED FROM FOOT PEDAL CONTROL SYSTEM
TO DEVICE ACTUATION UNIT FOR VARIABLE CONTROL OF A DEVICE

| HAND-HELD ID | MESSAGE LENGTH | DEVICE ACTUATION UNIT ID | VARIABLE ACTUATION CODE | COMMAND CODE | CHECKSUM |
|---|---|---|---|---|---|
| 11111111 | 00000110 | 00000001 | 11110000 | 00000001 | 11110010 |

*Figure 10*  180

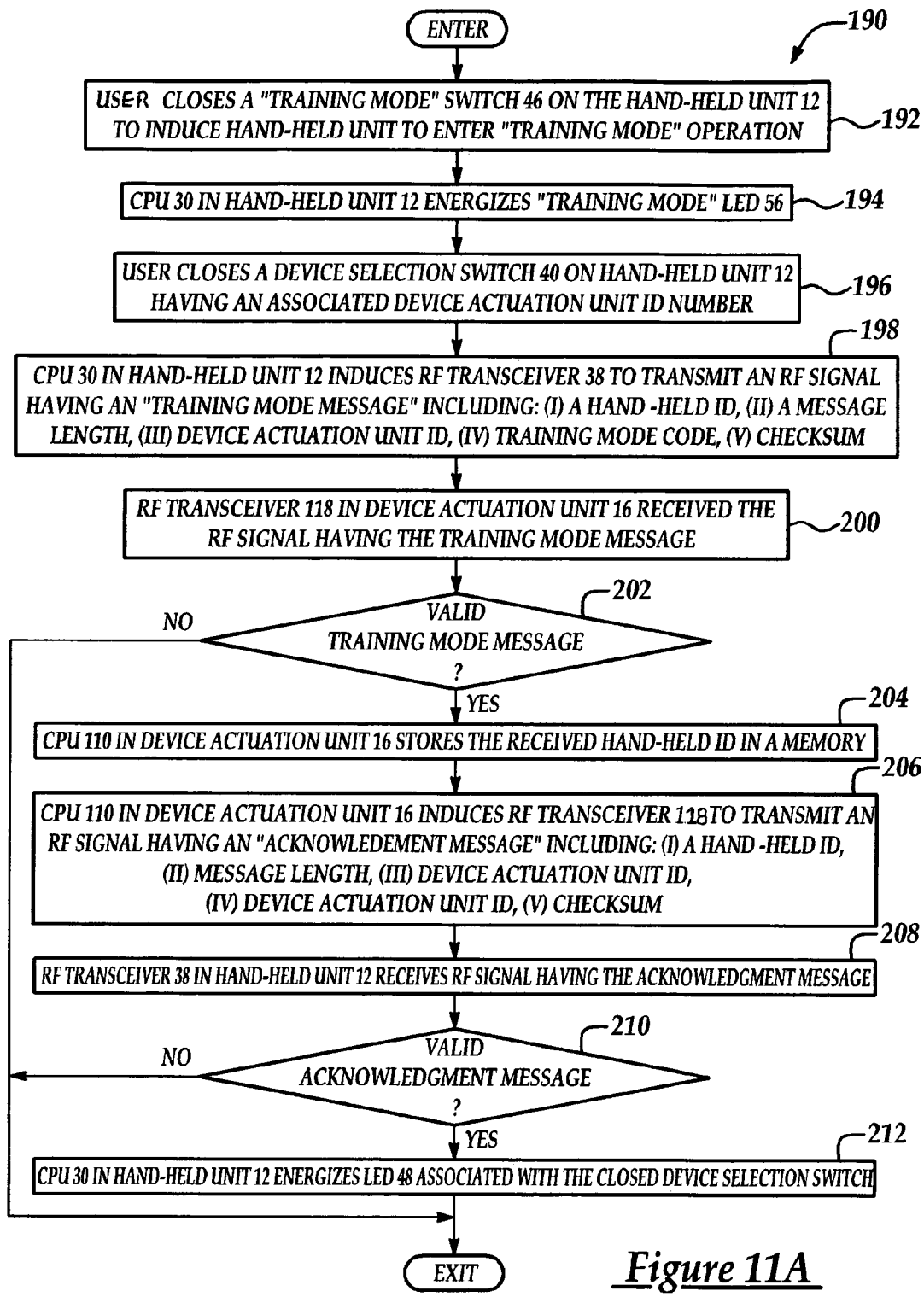

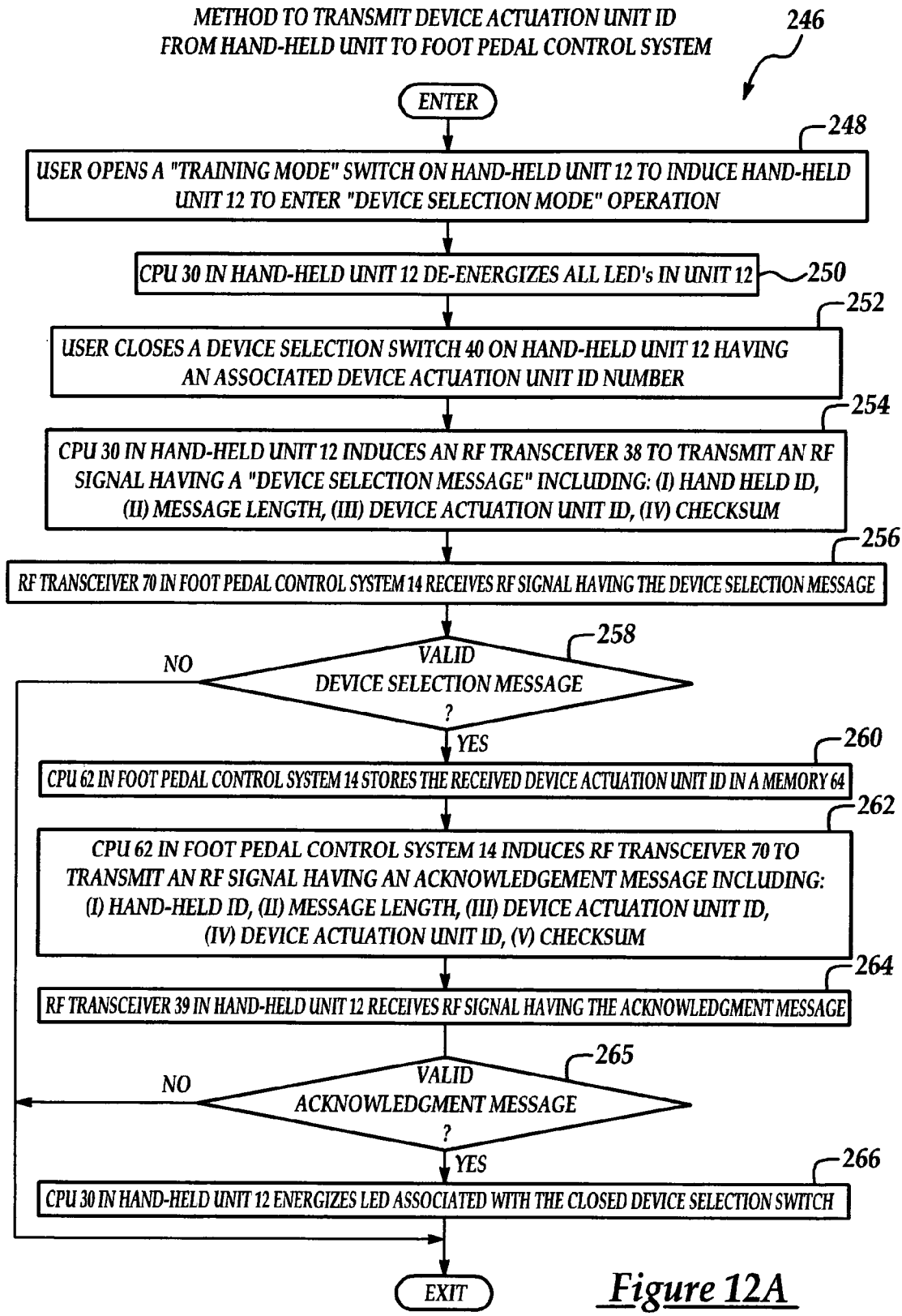

SYSTEM AND METHOD FOR REMOTELY CONTROLLING DEVICES

This application is a continuation-in-part of U.S. application Ser. No. 10/464,369, filed on Jun. 17, 2003 that claims priority to U.S. Provisional Ser. No. 60/389,229, filed on Jun. 17, 2002.

FIELD OF THE INVENTION

This invention relates to a system and method for the remotely controlling devices.

BACKGROUND OF THE INVENTION

Dental professionals generally utilize a plurality of dental devices when performing dental procedures on patients. Each device or implement is generally controlled using a foot pedal. Thus, a dental operatory room generally has a plurality of foot pedals located on the floor to allow the dentist to control the plurality of devices. The inventor herein has recognized that multiple foot pedals and their associated conduits and cords are a hindrance to the operator's mobility due to multitude of different foot pedals and their associated conduits and cords. Further, because the foot pedals are not standardized, each foot pedal often has a different level of control or "feel" such that the operator of the pedals fails to achieve a consistent level of control among the devices. Further, multiple foot pedals may cause confusion and increase the risk of an inadvertent activation of one of the foot pedals. Further, when a device associated with a foot pedal needs to be moved within an operatory room or between operatory rooms, an asepsis or contamination problem may occur. In particular, the operatory room floor and the foot pedal or cable associated with the foot pedal may not be sufficiently clean such that when the device is moved with the associated pedal, the pedal may undesirably contaminate the device.

Accordingly, the inventor herein has recognized that a need exists for an improved foot pedal control unit that reduces the number of foot pedals needed to control a plurality of dental or medical instruments.

SUMMARY OF THE INVENTION

The foregoing problems and limitations are reduced and/or eliminated by a system and a method for remotely controlling devices described herein.

A system for remotely controlling devices is provided. The system includes a foot pedal unit having a moveable member. The system further includes a transmitter operatively associated with the moveable member. The transmitter transmits a first signal in response to at least partial displacement of the moveable member when a first device is selected. The transmitter transmits a second signal in response to at least partial displacement of the moveable member when a second device is selected.

A method for remotely controlling devices is provided. The method includes transmitting a first signal in response to at least partial displacement of a moveable member on a foot pedal unit when a first device is selected. The method further includes transmitting a second signal in response to at least partial displacement of the moveable member on the foot pedal unit when a second device is selected. Finally, the method includes controlling the first device based on the first signal.

The system and method for remotely controlling devices provides a substantial advantage over other systems and methods. In particular, the system and method provide a foot pedal unit having one movable member that can be utilized to control multiple devices. Thus, an operator of the foot pedal unit can obtain a consistent control of multiple devices. Further, the single foot pedal unit can replace a plurality of other foot pedal providing for a less cluttered operatory floor.

BRIEF DESCRIPTION OF THE DRAWINGS

FIG. 5 is a schematic of a foot pedal unit having a rotatable movable member.

FIG. 6 is a schematic of a foot pedal unit having a linearly displaceable movable member.

FIG. 7A is a schematic of a "training mode message" transmitted from a handheld unit to a device actuation unit.

FIG. 7B is a schematic of an "acknowledgment message" transmitted from a device actuation unit to a handheld unit after device actuation unit receives a "training mode message".

FIG. 8A is a schematic of a "device selection message" transmitted from a handheld unit to a foot pedal control system to select a device.

FIG. 8B is a schematic of an "acknowledgment message" transmitted from a foot pedal control system to a handheld unit after the foot pedal control system receives a "device selection message."

FIG. 9 is a schematic of a "device actuation message" transmitted from a foot pedal control system to a device actuation unit for "on-off" control of the device.

FIG. 10 is a schematic of a "device actuation message" transmitted from a foot pedal control system to a device actuation unit for the "variable" control of the device.

FIGS. 11A-11C are flowcharts of a training method to transmit a Handheld ID from a handheld unit to a device actuation unit.

FIGS. 12A-12B are flowcharts of a method to transmit a Device Actuation Unit ID from a handheld unit to a foot pedal control system.

DETAILED DESCRIPTION OF EMBODIMENTS OF THE INVENTION

Figure 1:
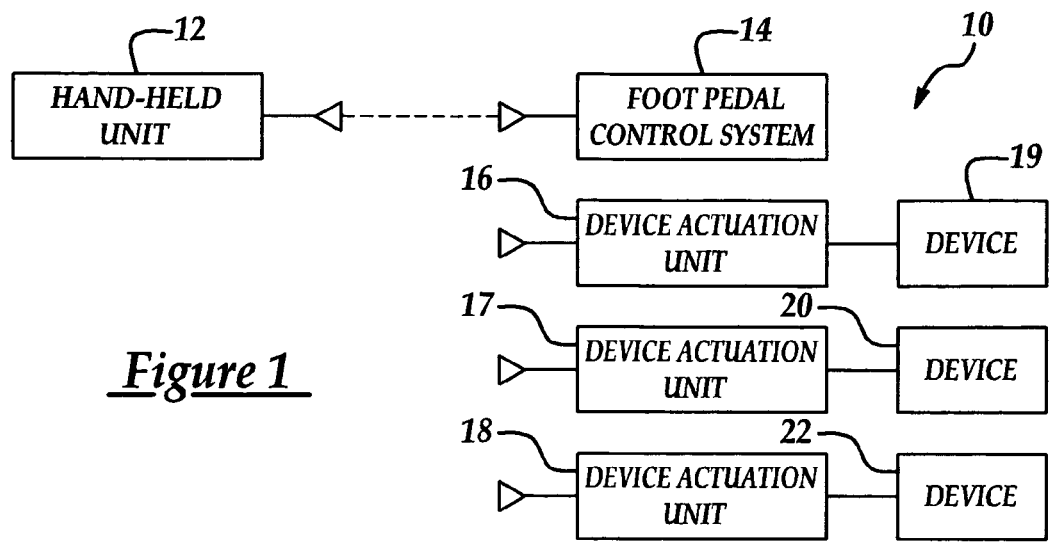
FIG. 1 is a schematic of a system for remotely controlling devices including a handheld transmitter unit, a foot pedal control system, and a device actuation unit.

Referring now to the Figures, like reference numerals are used to identify identical components in the various views. Referring to FIG. 1, a system 10 for remotely controlling devices is illustrated. System 10 may include a handheld unit 12, a foot pedal control system 14, and a device actuation unit 16. System 10 may further include a device actuation unit 17, a device actuation unit 18, and devices 19, 20, 22. Device actuation units 17, 18 may have a substantially similar hardware configuration as device actuation unit 16. Although, system 10 will be described as utilizing RF signals to communicate with the various system components, it should be noted that in alternate embodiments of system 10, infrared signals, near-infrared signals, or magnetic signals could be utilized for communicating with one or more of the various system components. It should be further noted that although only three device actuation units are illustrated in FIG. 1, a plurality of additional device actuation units (and devices attached thereto) could be controlled using foot pedal control system 14.

Handheld unit 12 is provided to transmit RF signals each having a "training mode message" including a Handheld ID associated with handheld unit 12. The "training mode messages" are transmitted to device actuation units 16, 17, 18 so that units 16, 17, 18 will respond to subsequent RF signals having messages containing the Handheld ID. Handheld unit 12 is also utilized to transmit an RF signal containing a "device selection message" to foot pedal control system 14 in order to select a specific device to be controlled by subsequent activation of foot pedal control system 14 by an operator. The foot pedal control system 14 is provided to transmit RF signals having a "device actuation message" including the Handheld ID to actuate a device connected to a predetermined device actuation unit. When the predetermined device actuation unit receives an RF signal having the "device actuation message" for the device actuation unit, the device actuation unit will actuate the device operably coupled to the device actuation unit.

Figure 2:
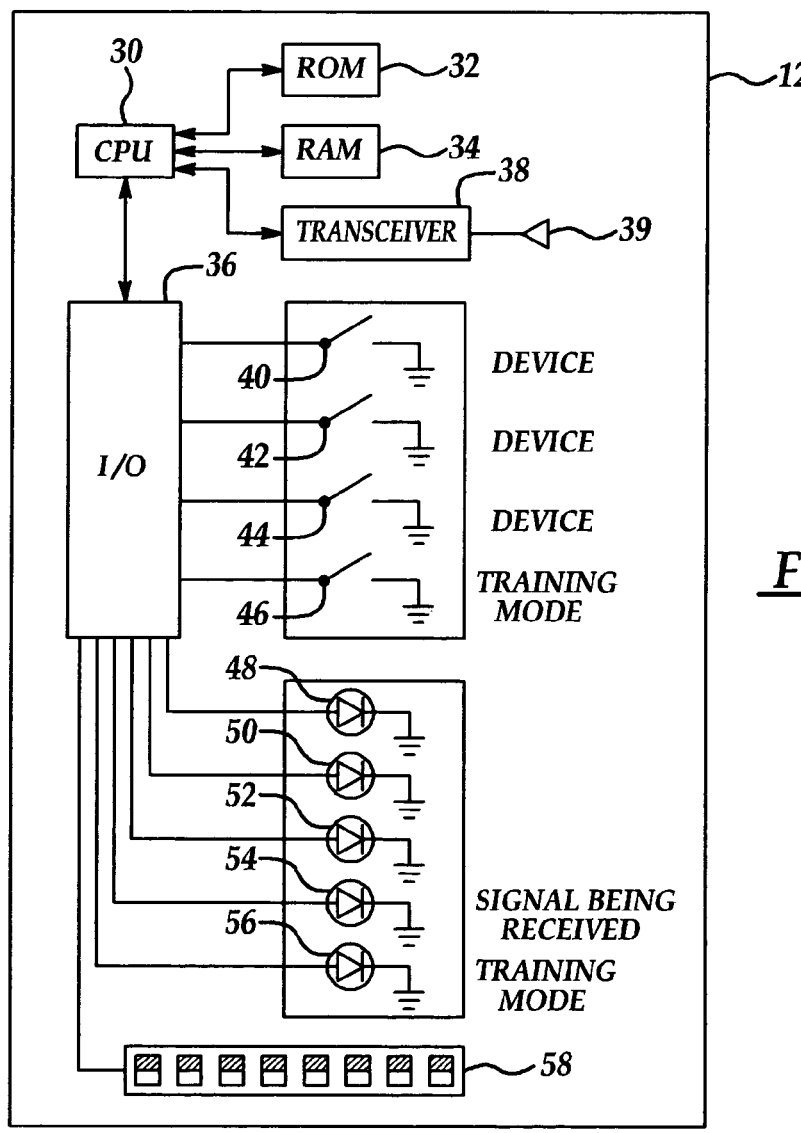
FIG. 2 is a detailed schematic of a handheld transmitter unit.

Referring to FIG. 2, handheld unit 12 will now be described in further detail. As shown, unit 12 may include a central processing unit (CPU) or microprocessor 30, read-only memory (ROM) 32, random access memory (RAM) 34, an input/output (I/O) interface 36, a transceiver 38, an antenna 39, normally-open switches 40, 42, 44, 46, light emitting diodes (LEDs) 48, 50, 52, 54, 56, and a Handheld ID DIP switch 58. CPU 30 of handheld unit 12 may be operably coupled to a battery (not shown) for supplying an operational voltage to CPU 30. An advantage of handheld unit 12 is that device actuation units to be controlled by a foot pedal control system can be selected by an operator using handheld unit 12 from any location within an operatory room. Another advantage of handheld unit 12 is that all of the communication between handheld unit 12 and the other system 10 devices are "wireless" communications thus eliminating any need for a plurality of communication wires from unit 12 to a plurality of devices to be trained or controlled.

Transceiver 38 is provided to transmit and receive RF signals via antenna 39. Thus, transceiver 38 operates as both an RF transmitter and an RF receiver. Transceiver 38 may receive and transmit RF signals in one or more frequency ranges (e.g., UHF, VHF, or microwave frequency). Further, transceiver 38 may modulate an RF signal containing a message using one or more modulation techniques (e.g., amplitude modulation (AM), frequency modulation (FM), frequency shift keying (FSK)) used by those skilled in the art. Further, transceiver 38 may transmit or pulse each RF signal for a predetermined time interval, such as 15 milliseconds for example. In an alternate embodiment, transceiver 38 could be replaced with an infrared transceiver (or infrared transmitter and/or infrared receiver) configured to transmit and receive infrared signals or near-infrared signals. In another alternate embodiment, transceiver 38 could be replaced with a magnetic transceiver (or magnetic transmitter and/or magnetic receiver) configured to transmit and receive magnetic signals.

In the illustrated embodiment, transceiver 38 may receive an RF signal containing a predetermined message and transmit a sequence of binary numbers representing the message to CPU 30. It should be noted that transceiver 38 could be replaced with a single RF transmitter if "handshaking" communication is not desired between (i) handheld unit 12 and the device actuation units, or (ii) handheld unit 12 and the foot pedal control system.

CPU 30 operates in a "training mode" when an operator closes training mode switch 46 and induces training mode LED 56 to emit light. Thereafter, when an operator closes one of selection switches 40, 42, 44 for selecting devices 19, 20, 22, respectively, CPU 30 induces transceiver 38 to transmit an RF signal having a "training mode message." Referring to FIG. 7A, a "training mode message" includes the following attributes: (i) a Handheld ID, (ii) a Message Length, (iii) a Device Actuation Unit ID, (iv) a Training Mode Code, and (v) a Checksum. The Handheld ID may correspond to an 8-bit number determined from DIP switch 58. In particular, CPU 30 reads the 8-bit number designated by the selector switch 58 to determine the Handheld ID and then stores the 8-bit number in ROM 32. For example, in FIG. 2, CPU 30 can read the value "11111111" designated by DIP switch 58 and then store the value "11111111" in ROM 32. The Handheld ID will be used as an identifier for subsequent communications between handheld unit 12, foot pedal control system 14, and device actuation units 16, 17, 18. The Message Length value corresponds to an 8-bit number representing the number of bytes of data in the "training mode message." The Training Mode Code corresponds to a unique number specifying that a transmitted message is a "training mode message." The Checksum value corresponds to a calculated checksum based on the Device Actuation Unit ID and the Training Mode Code—for checking the accuracy of a transmitted "training mode message." In particular, the Checksum value may be determined by adding together the Device Actuation Unit ID and the Training Mode Code.

Referring to FIG. 2, distinct addresses (i.e., Device Actuation Unit IDs) may be stored in ROM 32 for each of switches 40, 42, 44. For example, switches 40, 42, 44 may have corresponding Device Actuation Unit ID's "00000001", "00000010", "00000011", respectively, that are stored in ROM 32. Thus, for example when CPU 30 is in a "training mode" operation and an operator closes switch 42, the transmitted "training mode message" would have a device actuation unit ID of "00000010."

CPU 30 operates in a "device selection mode" when training mode switch 46 is an open operational position. Thereafter, when an operator closes one of selection switches 40, 42, 44 for selecting devices 19, 20, 22, respectively, CPU 30 induces transceiver 38 to transmit an RF signal having a "device selection message" which will be received by foot pedal control system 14. Referring to 8A, the "device selection message" includes the following attributes: (i) a Handheld ID, (ii) Message Length, (iii) Device Actuation Unit ID, and (v) Checksum. The Checksum value in the "device selection message" is identical to the Device Actuation Unit ID.

CPU 30 can induce LEDs 48, 50, 52 to emit light when selection switches 40, 42, 44, respectively, are in a closed operational position. CPU 30 induces LED 54 to emit light when a valid RF signal is being received by transceiver 38. CPU 30 induces LED 56 to emit light when the training mode switch 46 is in a closed operational position.

Figure 3:
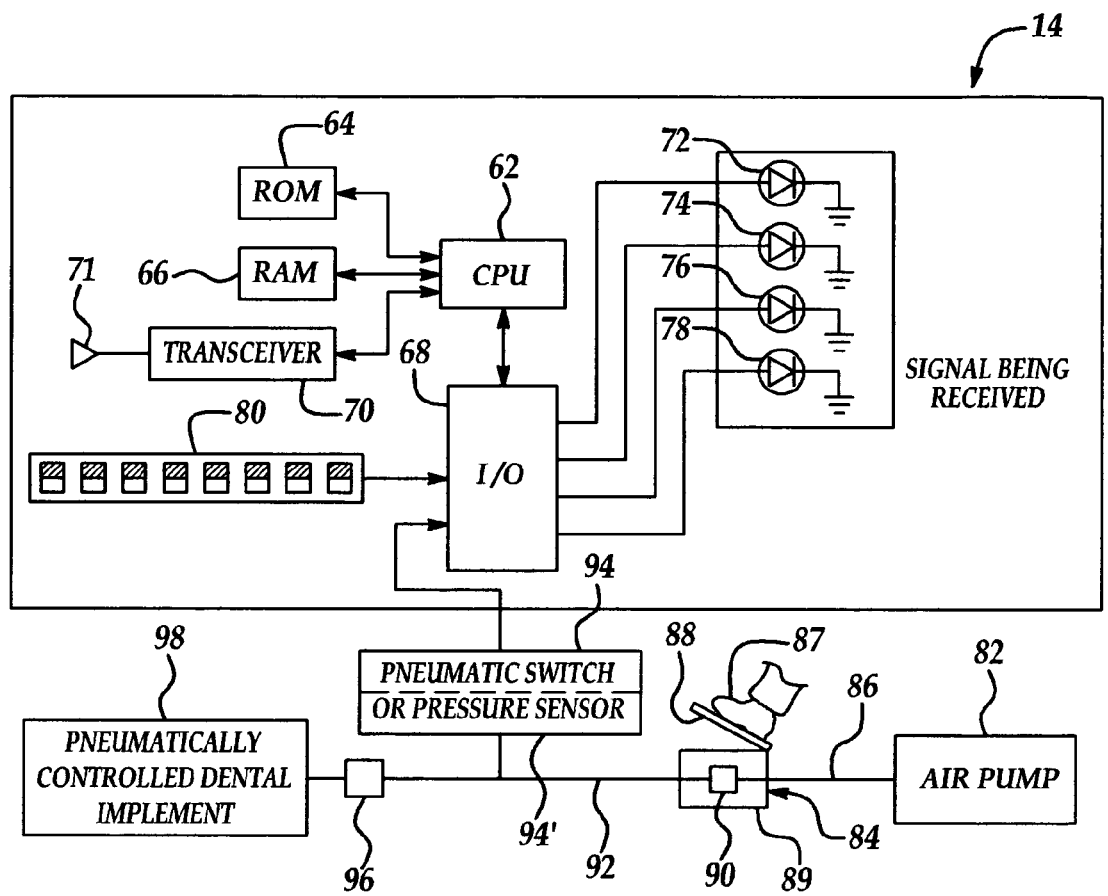
FIG. 3 is a detailed schematic of a first embodiment of a foot pedal control system.

Referring to FIG. 3, foot pedal control system 14 will now be described in further detail. Foot pedal control system 14 is provided to transmit RF signals each having a "device actuation message," including the Handheld ID, to actuate a device connected to a predetermined device actuation unit. As shown, foot pedal control system 14 includes a CPU 62, ROM 64, RAM 66, (I/O) interface 68, a transceiver 70, an antenna 71, light emitting diodes (LEDs) 72, 74, 76, 78, a Handheld ID DIP switch 80, an air pump 82, a foot pedal unit 84, a pneumatic switch or pressure sensor 94, a pneumatically controlled dental implement 98, a valve 96, and conduits 86, 92. CPU 62 of foot pedal control system 14 may be operably coupled to a battery (not shown) for supplying an operational voltage to CPU 62. An advantage of foot pedal control system 14 is that all of the communication between foot pedal control system 14 and the other system 10 devices are "wireless" communications thus eliminating any need for a plurality of communication wires from foot pedal control system 14 to a plurality of devices to be controlled.

Transceiver 70 is provided to transmit and receive RF signals via antenna 71. Thus, transceiver 70 operates as both an RF transmitter and an RF receiver. Transceiver 70 may receive and transmit RF signals in one or more frequency ranges (e.g., UHF, VHF, or microwave frequency). Further, transceiver 70 may modulate an RF signal containing a message using one or more modulation techniques (e.g., amplitude modulation (AM), frequency modulation (FM), frequency shift keying (FSK)) used by those skilled in the art. Further, transceiver 70 may transmit or pulse each RF signal for a predetermined time interval, such as 15 milliseconds for example. In an alternate embodiment, transceiver 70 could be replaced with an infrared transceiver (or infrared transmitter and/or infrared receiver) configured to transmit and receive infrared signals or near-infrared signals. In another alternate embodiment, transceiver 70 could be replaced with a magnetic transceiver (or magnetic transmitter and/or magnetic receiver) configured to transmit and receive magnetic signals. In the illustrated embodiment, transceiver 70 may receive an RF signal containing a predetermined message and transmit a sequence of binary numbers representing the message to CPU 62. It should be noted that transceiver 70 could be replaced with a single RF transmitter if "handshaking" communication is not desired between foot pedal control system 14 and handheld unit 12.

Distinct addresses (i.e., Device Actuation Unit IDs) may be stored in ROM 64 for each of LEDs 72, 74, 76. For example, LEDs 72, 74, 76 may have associated Device Actuation Unit ID's "00000001", "00000010", "00000011", respectively that are stored in ROM 64. Thus, when CPU 62 receives a "device selection message" containing a Device Actuation Unit ID from handheld unit 12, a corresponding LED will emit light. For example, when CPU 62 receives a "device selection message" containing a device actuation unit ID equal to "00000001", CPU 62 can induce LED 72 to emit light. Further, CPU 62 can induce LED 78 to emit light when transceiver 70 is receiving an RF signal.

Referring to FIGS. 8A, 8B, when CPU 62 receives a valid "device selection message" from handheld unit 12, CPU 62 will generate an "acknowledgment message." The "acknowledgment message" contains the following attributes: (i) a Handheld ID, (ii) Message Length, (iii) Device Actuation Unit ID, and (iv) Checksum. The Checksum value in the "acknowledgment message" is equal to the Device Actuation Unit ID value. For example, after receiving a valid "device selection message" 174, CPU 62 can induce transceiver 70 to transmit an RF signal containing the "acknowledgment message" 176 to handheld unit 12.

Referring to FIG. 3, Handheld ID DIP switch 80 is provided to select the Handheld ID that foot pedal control system 14 will respond to. For example, DIP switch 80 may be set to an 8-bit value of "11111111" corresponding to a Handheld ID. Thus, the Handheld ID specified by DIP switch 80 foot of pedal control system 14 should be equal to the Handheld ID specified by DIP switch 58 of handheld unit 12.

The remaining components of foot pedal control system 14 will now be explained. Foot pedal unit 84 is provided to detect at least partial displacement of movable member 88 by an operator. Foot pedal control unit 84 may further include a housing 89, a movable member 88, and a pneumatic valve 90. Foot pedal unit 84 is connected to an air pump 82 via a conduit 86. Air pump 82 supplies pressurized air at a predetermined pressure through conduit 86 to pneumatic valve 90. Foot pedal unit 84 is further operatively coupled to a conduit 92 that extends to a pneumatic valve 96 that is further coupled to a pneumatically controlled dental implement 98. Further, a pneumatic switch 94 or a pressure sensor 94' may be operatively coupled to conduit 92. The switch 94 or pressure sensor 94' may transmit a signal to I/O interface 68 that is measured or read by CPU 62.

When a foot 87 of an operator displaces movable member 88, pneumatic valve 90 may open to propagate pressurized air from air pump 82 to pneumatic valve 96 for driving dental implement 98. Valve 96 only opens when an operator removes dental implement 98 from a holding fixture. The inventor herein has recognized that foot pedal control unit 84 may be further utilized to control a plurality of other devices. When at least partial displacement of movable member 88 opens or partially opens pneumatic valve 90, pneumatic switch 94 may detect the opening and generate a signal. The signal induces CPU 62 to generate a "device actuation message." Alternately, when a pressure sensor 94' is utilized which generates a pressure signal indicative of the pressure in conduit 92, CPU 62 may generate the "device actuation message" when the pressure is greater than or equal to a predetermined pressure. It should be noted that the pressure in conduit 92 will be greater than or equal to the predetermined pressure displacement of movable member 88 at least partially opens valve 90. After generating the "device actuation message", CPU 62 may induce transceiver 70 to transmit an RF signal containing the "device actuation message" to a device actuation unit.

An advantage of foot pedal control unit 84 is that a single movable member 88 (on a single foot pedal unit) can be utilized to selectively control a plurality of device actuation units and associated devices coupled to the device actuation units. Thus, other foot pedal units having a plurality of movable members or pedals for controlling a plurality of devices are no longer needed. Thus, with foot pedal control unit 84, dental or medical professionals will not have to "search" for the correct pedal from a plurality of pedals with their feet to actuate a desired device, as done with other foot pedal units having a plurality of foot pedals. Further, a plurality of other foot pedal units each having a pedal for controlling a distinct device will no longer be needed. Thus, because foot pedal control unit 84 can replace a plurality of other foot pedal units, unit 84 will provide for a less cluttered operatory floor. Further, dental or medical professionals using foot pedal unit 84 can obtain a consistent "feel" or depression force for controlling multiple devices.

Referring to FIG. 9, the "device actuation message" transmitted in an RF signal from the foot pedal control system 16 may contain the following attributes: (i) a Handheld ID, (ii) Message Length, (iii) Device Actuation Unit ID, (iv) Actuation Code, and (v) Checksum. The Checksum value may be determined by adding the Device Actuation Unit ID and the Actuation Code. For example, foot pedal control system 14 may transmit device actuation message" 178 to device actuation unit 16 to control device 19.

Figure 4:
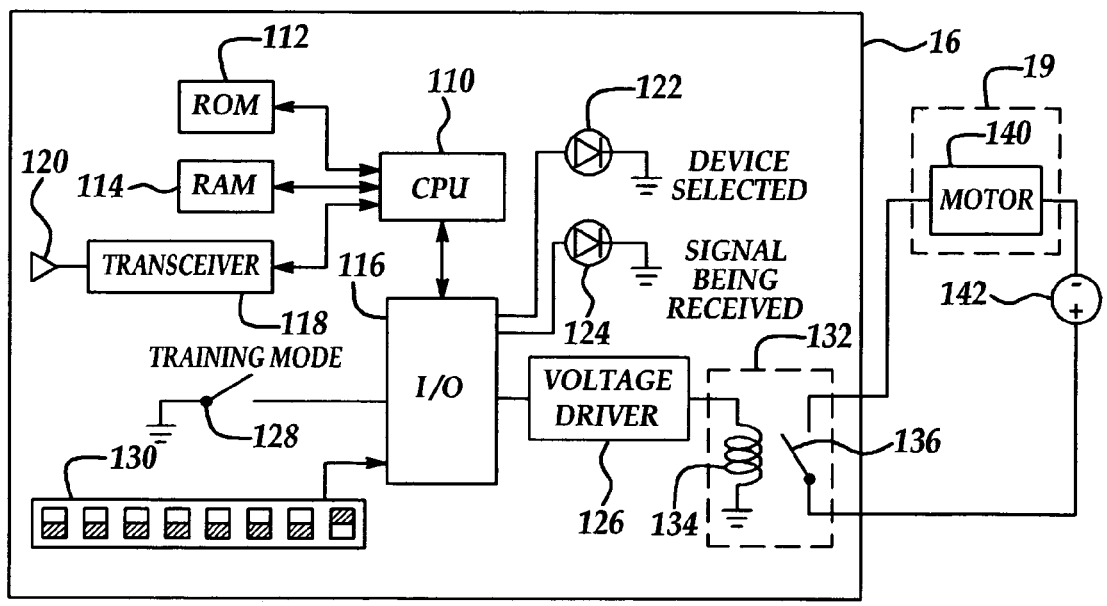
FIG. 4 is a detailed schematic of a first embodiment of a device actuation unit.

Referring to FIG. 4, device actuation unit 16 will now be described in further detail. Device actuation unit 16 is provided to actuate a device, such as a dental or medical device for example, operatively coupled to unit 16. As shown, device actuation unit 16 may include a CPU 110, ROM 112, RAM 114, I/O interface 116, a transceiver 118, an antenna 120, a training mode switch 128, Device Actuation ID DIP switch 130, LEDs 122, 124, a voltage driver 126, and a relay 132. CPU 110 of device actuation unit 16 may be operably coupled to a battery (not shown) for supplying an operational voltage to CPU 110. An advantage of using device actuation unit 16 is that unit 16 can be moved with an operably coupled device to be controlled, from a first room to a second room, without the need for moving foot pedal control system 14. Thereafter, device actuation unit 16 could be programmed to respond to another hand-held unit and another foot pedal control system 14 in the second room. Thus, device actuation unit 16 prevents contamination of other devices by allowing an operator to move device actuation 16 and an operably coupled device without having to move or touch a potentially contaminated foot pedal control system 16. Another advantage of device actuation unit 16 is that device actuation unit 16 can be controlled using "wireless" communications thus eliminating any need for a plurality of communication wires to device actuation unit 16.

Transceiver 118 is provided to transmit and receive RF signals via antenna 120. Thus, transceiver 118 operates as both an RF transmitter and an RF receiver. Transceiver 118 may receive and transmit RF signals in one or more frequency ranges (e.g., UHF, VHF, or microwave frequency). Further, transceiver 118 may modulate an RF signal containing a message using one or more modulation techniques (e.g., amplitude modulation (AM), frequency modulation (FM), frequency shift keying (FSK)) used by those skilled in the art. Further, transceiver 118 may transmit or pulse each RF signal for a predetermined time interval, such as 15 milliseconds for example. In an alternate embodiment, transceiver 118 could be replaced with an infrared transceiver (or infrared transmitter and/or infrared receiver) configured to transmit and receive infrared signals or near-infrared signals. In another alternate embodiment, transceiver 118 could be replaced with a magnetic transceiver (or magnetic transmitter and/or magnetic receiver) configured to transmit and receive magnetic signals. In the illustrated embodiment, transceiver 118 may receive an RF signal containing a predetermined message and transmit a sequence of binary numbers representing the message to CPU 110. It should be noted that transceiver 118 could be replaced with a single RF transmitter if "handshaking" communication is not desired between device actuation unit 16 and handheld unit 12.

Voltage driver 126 is provided to generate a voltage for actuating a relay 132 coupled to device 19. In particular, voltage driver 126 is coupled to I/O interface 126 and is further coupled to a coil 134 of relay 132. Voltage driver 126 may receive a signal from CPU 110 via I/O interface 116 that induces driver 126 to generate a voltage sufficient to energize coil 134. In response, a contact 136 of relay 132 may move to a closed operating position to "turn on" or energize device 19.

DIP switch 130 is used to specify a Device Actuation Unit ID for device actuation unit 16. In particular, CPU 110 reads the 8-bit number designated by switch 130 to determine the Device Actuation Unit ID and then stores the 8-bit number in ROM 112. For example, referring to FIG. 4, CPU 110 can read the value "00000001" designated by selector switch 130 and then store the value "00000001" in ROM 112.

LED 124 may be provided to indicate when device actuation unit 16 is receiving an RF signal having a valid "device actuation message" from foot pedal control system 14. In particular, CPU 110 induces LED 124 to emit light when transceiver 118 is receiving an RF signal having a valid "device actuation message" from foot pedal control system 14.

LED 122 may be provided to indicate when device actuation unit 16 receives a valid "device selection message" from handheld unit 12. In particular, CPU 110 induces LED 122 to emit light when transceiver 118 receives an RF signal having a valid "device selection" message from handheld unit 12.

Training mode switch 128 is provided to place CPU 110 into a "training mode" operation. In particular, when an operator closes switch 128, CPU 110 enters a "training mode" and awaits receipt of a "training mode message" from handheld unit 12. Referring to FIGS. 7A, 7B, when CPU 110 receives a valid "training mode message" (e.g. training mode message 170), the CPU 110 generates an acknowledgment message (e.g. acknowledgment message 172). The "acknowledgment message" contains the following attributes: (i) a Handheld ID, (ii) Message Length, (iii) Device Actuation Unit ID, (iv) Device Actuation Unit ID, and (v) Checksum. The Checksum value in the "acknowledgment message" is equal to twice the Device Actuation Unit ID value. Further, CPU 110 induces transceiver 118 to transmit an RF signal containing the "acknowledgment message" to handheld unit 12. CPU 110 also stores the Handheld ID from the valid "training mode message" in ROM 112 for verifying whether subsequent received messages are valid "device selection messages."

After device actuation unit 16 has been trained with a Handheld ID and the training mode switch 128 is moved to an open operating position, CPU 110 enters a "device actuation message receiving mode." In particular, when an operator opens switch 128, CPU 110 awaits an RF signal containing a "device actuation message" from foot pedal control system 14. Referring to FIG. 9, when a valid "device actuation message" is received by CPU 110 indicating that foot pedal control system 14 is instructing device actuation unit 16 to actuate device 19, CPU 110 induces voltage driver 126 to close contact 136 to "turn on" or energize device 19. Thereafter, CPU 110 continues to energize device 19 so long as a valid "device actuation message" is received from system 14 within predetermined time intervals. It should be further noted that contact 126 could also be utilized to control energization and de-energization of a pneumatic valve (not shown) or a hydraulic valve (not shown) for opening or closing a pneumatic valve or hydraulic valve, respectively, for further controlling operation of any pneumatically controlled device or hydraulically controlled device, respectively.

Referring to FIG. 1, devices 19, 20, 22 may comprise any electrically, pneumatically, magnetically, or hydraulically actuated device. For example, devices 19, 20, 22 may comprise electrically, pneumatically, magnetically, or hydraulically actuated medical or dental devices. Further, devices 19, 20, 22 may comprise one or more of the following devices: a drill, a dental chair whose chair position can be adjusted automatically, an infrared photo-optic imaging camera, a dental irrigator, an intra-oral camera, a laser, an air-abrasion unit, an electro-surgery unit, an ultrasonic teeth cleaning unit, a piezo-ultrasonic unit, an air polishing prophylaxis device, a gum depth measurement probe, a surgical microscope, a microprocessor controlled anesthetic delivery system, and an endodontic heat source device.

For example, a drill useable with the inventive control system includes the torque control motor drill sold under the trademark Tecnika and is manufactured by Advanced Technology Research (ATR), located at Via del Pescino, 6, 51100

Pistoia, Italy, and sold in the United States by Dentsply Tulsa Dental at 5001 E. 68$^{th}$, Tulsa, Okla. 74136-3332. Further, it should be noted that the inventive control system could be used to control operation of any electrically controlled or pneumatically controlled drill.

For example, a dental chair usable with the inventive control system includes the dental chair sold under the trademark Priority® manufactured by A-DEC located at 2601 Crestview Drive, Newberg, Oreg., which provides elevational control of the chair, tilting of the back of the chair, and memory recall positions. Thus, the elevation position, tilting position, and other variable position adjustments could be controlled by the inventive control system. Further, it should be noted that the inventive control system could be used to control operation of any electrically controlled or hydraulically controlled dental chair or control unit associated with the dental chair.

For example, an infrared photo-optic imaging camera that may be utilized with the inventive control system includes a camera sold under the trademark CEREC® manufactured by Sirona Dental Systems located at Fabrikstrabe 31, 64625 Bensheim, Hessen, Germany, and sold in the United States by Patterson Dental Supply, Inc., located at 1031 Mendota Heights Rd., Saint Paul, Minn. 55120. Further, it should be noted that the inventive control system could be used to control any imaging camera that can be automatically or externally controlled to generate a digital image or a film image.

For example, a dental irrigator that may be utilized with the inventive control system includes a dental irrigator sold under the trademark Piezon® Master 600, manufactured by Electro Medical Systems located at 12092 Forestgate Drive, Dallas Tex., 75243. Further, it should be noted that the inventive control system could be used to control operation of any dental irrigator or dental irrigator control system that directs fluid under pressure therethrough.

For example, an intra-oral camera that may be utilized with the inventive control system includes an intra-oral camera sold under the trademark Prism™, manufactured by Professional Dental Technologies, Inc., located at 2410 Harrison Street, Batesville, Ark. 72501, or the AcuCam® Concept IV manufactured by Gendex, a division of Dentsply International located at 901 W. Oakton St., Des Plains, Ill. 60018-1884. Further, it should be noted that the inventive control system could be used to control operation of any intra-oral camera (or video capture card or video capture computer associated with the camera) to generate, store, retrieve, display, or print a digital or analog video image.

For example, a laser unit that may be utilized with the inventive control system includes a laser sold under the trademark Odyssey™, manufactured by Ivoclar Vivadent Inc., located at 175 Pineview Drive, Amherst, N.Y. 14228. Alternately, the system could be utilized with a laser sold under the trademark Waterlase®, manufactured by Biolase Technology, Inc., located at 981 Calle Amanecer, San Clemente, Calif. 92673. Further, it should be noted that the inventive control system could be used to control operation of any other known laser.

For example, an air-abrasion unit that may be utilized with the inventive control system includes an air-abrasion unit sold under the trademark PrepStart™, manufactured by Danville Engineering, located at 2021 Omega Road, San Ramon Calif. 94583. Further, it should be noted that the inventive control system could be used to control operation of any other type of air-abrasion unit utilized in dental procedures, in medical procedures, or during processing or cleaning of manufactured goods.

For example, an electro-surgery unit that may be utilized with the inventive control system includes the electro-surgery unit sold under the trademark Hyfrecator® 2000, manufactured by ConMed® Corporation, located at 310 Broad Street, Utica, N.Y. 13501. Further, it should be noted that the inventive control system could be used to control operation of any other electro-surgery unit that utilizes electrical energy for removing tissue or bone.

For example, an ultrasonic teeth cleaning unit that may be utilized with the inventive control system includes the teeth cleaning unit sold under the trademark Cavitron® 3000 manufactured by Dentsply International located at 901 W. Oakton Street, Des Plains, Ill. 60018-1884. Further, it should be noted that the inventive control system could be used to control operation of any other ultrasonic teeth cleaning unit.

For example, a piezo-ultrasonic unit that may be utilized with the inventive control system includes the piezo-ultrasonic unit sold under the trademark Spartan MTS™, manufactured by Obtura Spartan located at 1663 Fenton Business Park Court, Fenton, Mo. 63026. Further, it should be noted that the inventive control system could be used to control operation of any other piezo-ultrasonic unit that agitates or vibrates a tip for cleaning teeth or removing tooth structure. Piezo-ultrasonic units may have fluid cooled tips.

For example, an air polishing prophylaxis device that may be utilized with the inventive control system includes the air polishing prophylaxis device sold under the trademark Cavitron® Prophy-Jet®, manufactured by Dentsply International located at 901 W. Oakton Street, Des Plains, Ill. 60018-1884. Further, it should be noted that the inventive control system could be used to control operation of any other air polishing prophylaxis device that uses compressed air for delivering a fluid and/or an abrasive compound out of a nozzle for cleaning teeth and gums.

For example, the gum depth measurement probe that may be utilized with the inventive control system includes the gum depth measurement probe sold under the trademark Florida Probe®, manufactured by Florida Probe Corporation, located at 3700 NW 91$^{st}$ Street, Suite C-100, Gainesville, Fla. 32606. Further, it should be noted that the inventive control system could be used to control operation of any other gum depth measurement probe that can be automatically or externally controlled to take a gum depth measurement.

For example, a surgical microscope that may be utilized with the inventive control system includes the surgical microscope sold under the trademark OPMI® pico, manufactured by Carl Zeiss Surgical Inc., located at One Ziess Drive, Thornwood, N.Y. 10594. Alternately, the inventive control system could utilized with the surgical microscope sold under the trademark Protégé™, manufactured by Global Surgical Corporation, located at 3610 Tree Court Industrial Blvd., St. Louis, Mo. 63122-6622. Further, it should be noted that the inventive control system could be used to control operation of any other surgical microscope that includes one or more of: automatically controllable height adjustment, automatically controllable focusing, automatically controllable field of view size, viewing lights, and a camera associated with the surgical microscope.

For example, a microprocessor-controlled anesthetic delivery system that may be utilized with the inventive control system includes the anesthetic delivery system sold under the trademark The Wand™ II, manufactured by the Dental Division of Milestone Scientific located at 151 S. Pfingsten Road, Deerfield, Ill. 60015. Further, it should be noted that the inventive control system could be used to control operation of any other microprocessor-controlled anesthetic delivery system that delivers predetermined amounts of an anesthetic to a medical or dental patient.

For example, an endodontic heat source device that may be utilized with the inventive control system includes the endodontic heat source device sold under the trademark System B HeatSource™ model 1005, manufactured by Analytic-Sybron Dental Specialties located at 1332 South Lone Hill Avenue, Glendora, Calif. 91740. Further, it should be noted that the inventive control system could be used to control operation of any other endodontic heat source device.

Referring to FIG. 4, although device 19 could comprise any one of the foregoing plurality of described devices, for purposes of discussion, device 19 will comprise an electrically actuated drill. Drill 19 may include a motor 140 electrically coupled to a low-voltage source 142 and electrical contact 136. Upon closure of electrical contact 136, voltage source 142 energizes motor 140 to rotate or reciprocate a drill bit (not shown) or a root canal file.

Referring to FIG. 11A, a method 190 for transmitting a Handheld Unit ID from handheld unit 12 to device actuation unit 19 will now be described. At step 192, an operator of handheld unit 12 closes training mode switch 46 on handheld unit 12 to induce unit 12 to enter "training mode."

At step 194, CPU 30 in handheld unit 12 energizes LED 56.

At step 196, the operator closes device selection switch 40 on handheld unit 12 having an associated Device Actuation Unit ID Number (e.g., "00000001").

At step 198, in response to the closure of switch 40, CPU 30 induces RF transceiver 38 to transmit an RF signal having a "training mode message" including: (i) Handheld ID, (ii) Message Length, (iii) Device Actuation Unit ID, (iv) Training Mode Code, and (v) Checksum.

At step 200, RF transceiver 118 in device actuation unit 16 receives the RF signal having the "training mode message."

At step 202, CPU 110 in unit 16 determines whether the received "training mode message" is a valid message. If the value of step 202 equals "yes", the method advances to step 204. Otherwise, the method 190 is exited.

At step 204, CPU 110 stores the received Handheld ID in ROM 112.

At step 206, CPU 110 induces RF transceiver 118 to transmit an RF signal having an "acknowledgment message" including: (i) a Handheld ID, (ii) Message Length, (iii) Device Actuation Unit ID, (iv) Device Actuation Unit ID, and (v) Checksum.

At step 208, RF transceiver 38 in handheld unit 12 receives the RF signal having the "acknowledgment message" from device actuation unit 16.

At step 210, CPU 30 in handheld unit 12 makes a determination as to whether the received "acknowledgment message" was a valid acknowledgment message. If the value of step 210 equals "yes", the method advances to step 212. Otherwise, the method returns to step 202.

At step 212, CPU 30 in handheld unit 12 energizes LED 48 indicating that (i) the Device Actuation Unit ID associated with switch 40 (and stored in ROM 32) matches the Device Actuation Unit ID selected by DIP switch 130 of device actuation unit 16, and (ii) unit 16 stored the Handheld ID contained in the received "training mode message." After step 212, the method 190 is exited.

Figure 11B:
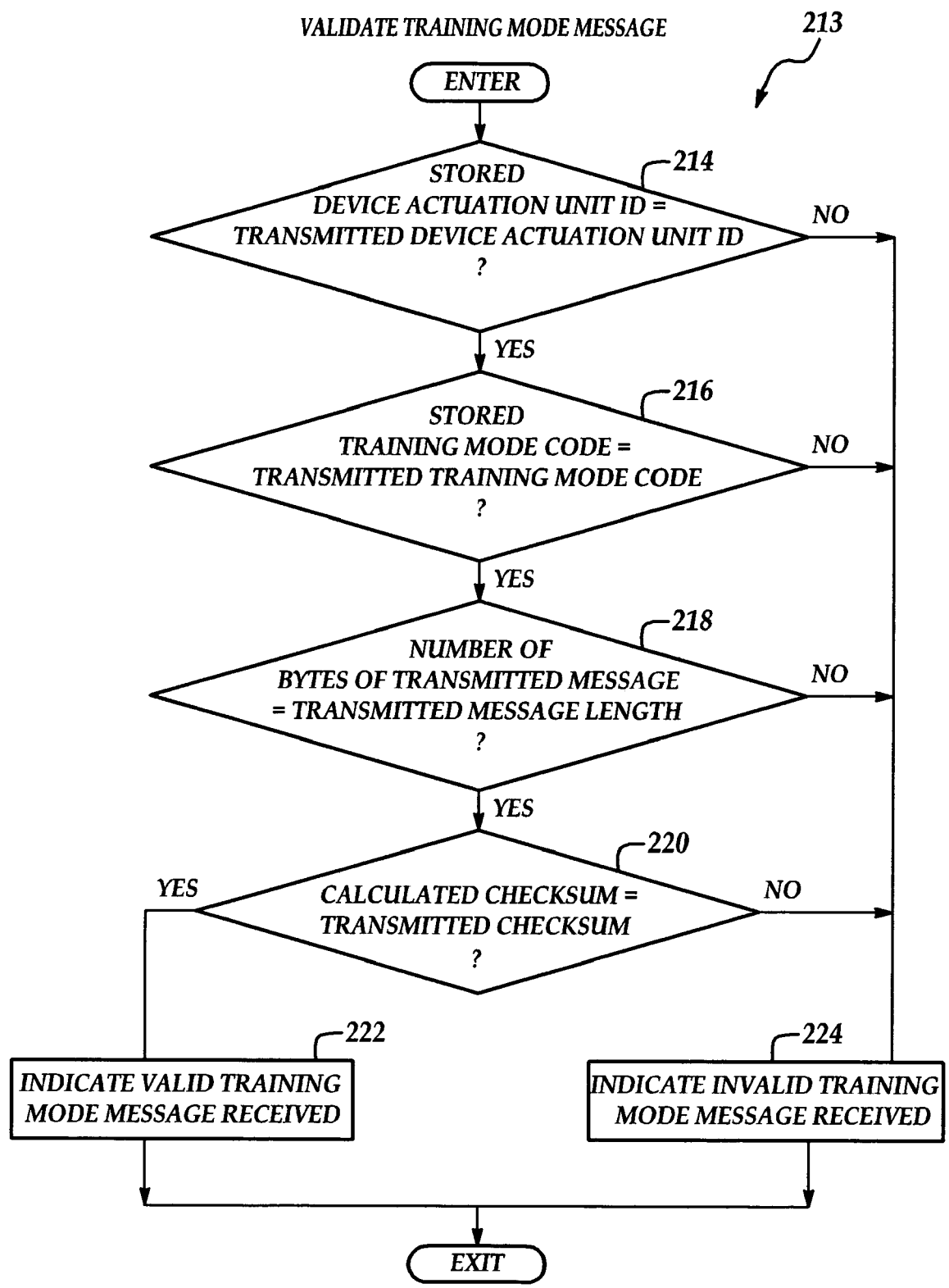

Referring to FIG. 11B, the method 213 for implementing step 202 for determining whether a valid "training mode message" was received by device actuation unit 16 will now be explained. In particular, step 202 may be implemented using the steps 214-224. At step 214, CPU 110 makes a determination as to whether a Device Actuation Unit ID stored in ROM 112 equals the Device Actuation Unit ID contained in the received "training mode message". If the value of step 214 equals "yes", the method advances to step 216. Otherwise, the method advances to step 224 that indicates an invalid "training mode message" was received.

At step 216, CPU 110 makes a determination as to whether a Training Mode Code stored in ROM 112 equals the Training Mode Code contained in the received "training mode message." If the value of step 216 equals "yes", the method advances to step 218. Otherwise, the method advances to step 224

At step 218, CPU 110 makes a determination as to whether the number of bytes of the transmitted message equals the Message Length value contained in the received "training mode message."

If the value of step 216 equals "yes", the method advances to step 220. Otherwise, the method advances to step 224.

At step 220, CPU 110 makes a determination as to whether the checksum calculated from the received "training mode message" equals the Checksum value contained in the received "training mode message." If the value of step 220 equals "yes", CPU 110 indicates that a valid "training mode message was received. In particular, CPU 110 may set a internal memory flag equal to a logical "1" value. Otherwise, the method advances to step 224 where CPU 110 indicates that an invalid "training mode message" was received.

Figure 11C:
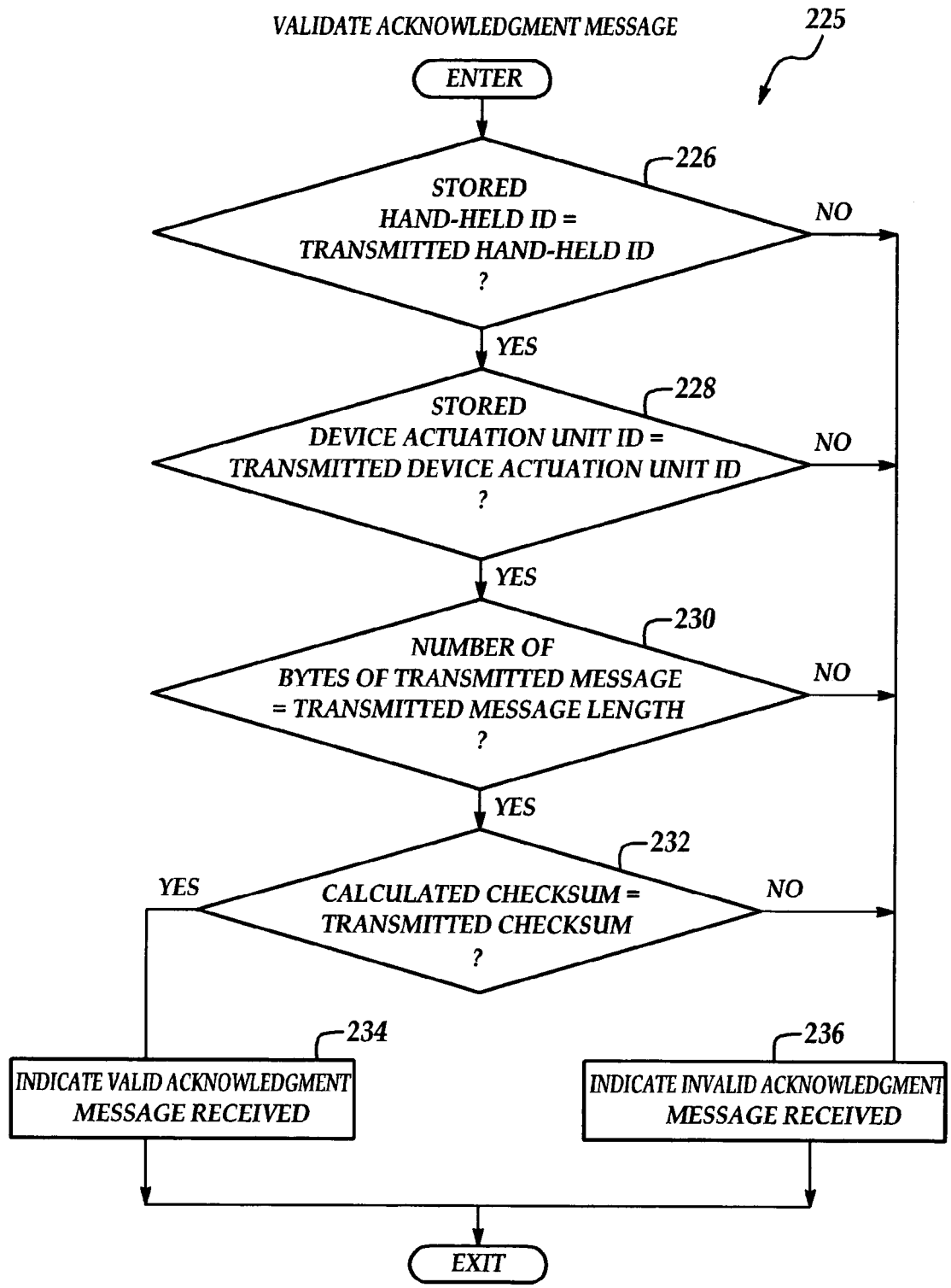

Referring to FIG. 11C, the method 225 for implementing step 210 for determining whether a valid "acknowledgment message" was received by handheld unit 12 from device actuation unit 16 will now be explained. At step 226, CPU 30 in handheld unit 12 makes a determination as to whether a Handheld ID stored in ROM 32 equals the Handheld ID contained in the received "acknowledgment message." If the value of step 226 equals "yes", the method advances to step 228. Otherwise, the method advances to step 236 that indicates an invalid "acknowledgment message" was received by handheld unit 12.

At step 228, CPU 30 makes a determination as to whether a Device Actuation Unit ID stored in ROM 32 equals the Device Actuation Unit ID contained in the received "acknowledgment message". If the value of step 228 equals "yes", the method advances to step 230. Otherwise, the method advances to step 236.

At step 230, CPU 30 makes a determination as to whether the number of bytes of the transmitted in the "acknowledgment message" equals the Message Length value contained in the received "acknowledgment message." If the value of step 230 equals "yes", the method advances to step 232. Otherwise, the method advances to step 236.

At step 232, CPU 30 makes a determination as to whether the checksum calculated by CPU 30 based on the received "acknowledgment message" equals the Checksum value contained in the "acknowledgment message." If the value of step 232 equals "yes", CPU 30 indicates that a valid "acknowledgment message" was received. In particular, CPU 30 may set a internal memory flag equal to a logical "1" value. Otherwise, the method advances to step 236 where CPU 30 indicates that an invalid "acknowledgment message" was received.

Referring to FIG. 12A, a method for transmitting a Device Actuation Unit ID from handheld unit 12 to foot pedal control system 14 will now be explained. In other words, the method for selecting a device to be controlled by foot pedal control system 14 will be explained. At step 248, an operator opens "training mode" switch 46 on handheld unit 12 to induce CPU 30 to enter into a "device selection mode" operation.

At step 250, CPU 30 de-energizes LED's 48, 50, 52, 54, 56.

At step 252, an operator closes device selection switch 40 on handheld unit 12 having associated Device Actuation Unit ID number (e.g., "00000001"). At step 254, in response to the closure of switch 40, CPU 30 induces RF transceiver 38 to transmit an RF signal having a "device selection message" including: (i) a Handheld ID, (ii) Message Length, (iii) Device Actuation Unit ID, and (v) Checksum. The Checksum value in the "device selection message" is identical to the Device Actuation Unit ID. For example, transceiver 38 could transmit an RF signal having device selection message 174.

At step 256, RF transceiver 70 in foot pedal control system 14 receives the RF signal having the "device selection message" from handheld unit 12.

At step 258, CPU 62 in foot pedal control system 14 makes a determination as to whether the "device selection message" was a valid message. If the value of step 258 equals "yes", the method advances to step 260. Otherwise, the method 246 is exited.

At step 260, CPU 62 stores the received Device Actuation Unit ID from the "device selection message" in ROM 64.

At step 262, CPU 62 induces RF transceiver 70 to transmit an RF signal having an "acknowledgment message" including: (i) a Handheld ID, (ii) Message Length, (iii) Device Actuation Unit ID, (iv) Device Actuation Unit ID, and (v) Checksum. For example, transceiver 70 could transmit an RF signal having "acknowledgement message" 176.

At step 264, RF transceiver 38 in handheld unit 12 receives the RF signal having the "acknowledgment message" from unit 14

At step 265, CPU 30 in handheld unit 12 makes determination as to whether a valid "acknowledgment message" was received. It should be noted that step 265 may be implemented using the method 225 of FIG. 11C. If the value of step 265 equals "yes", the method advances to step 266. Otherwise, the method 246 is exited.

At step 266, CPU 30 in handheld unit 12 energizes LED 48 indicating that foot pedal controls system 14 has "learned" the Device Actuation Unit ID associated with switch 40 of handheld unit 12. After step 266, the method 246 is exited.

Figure 12B:
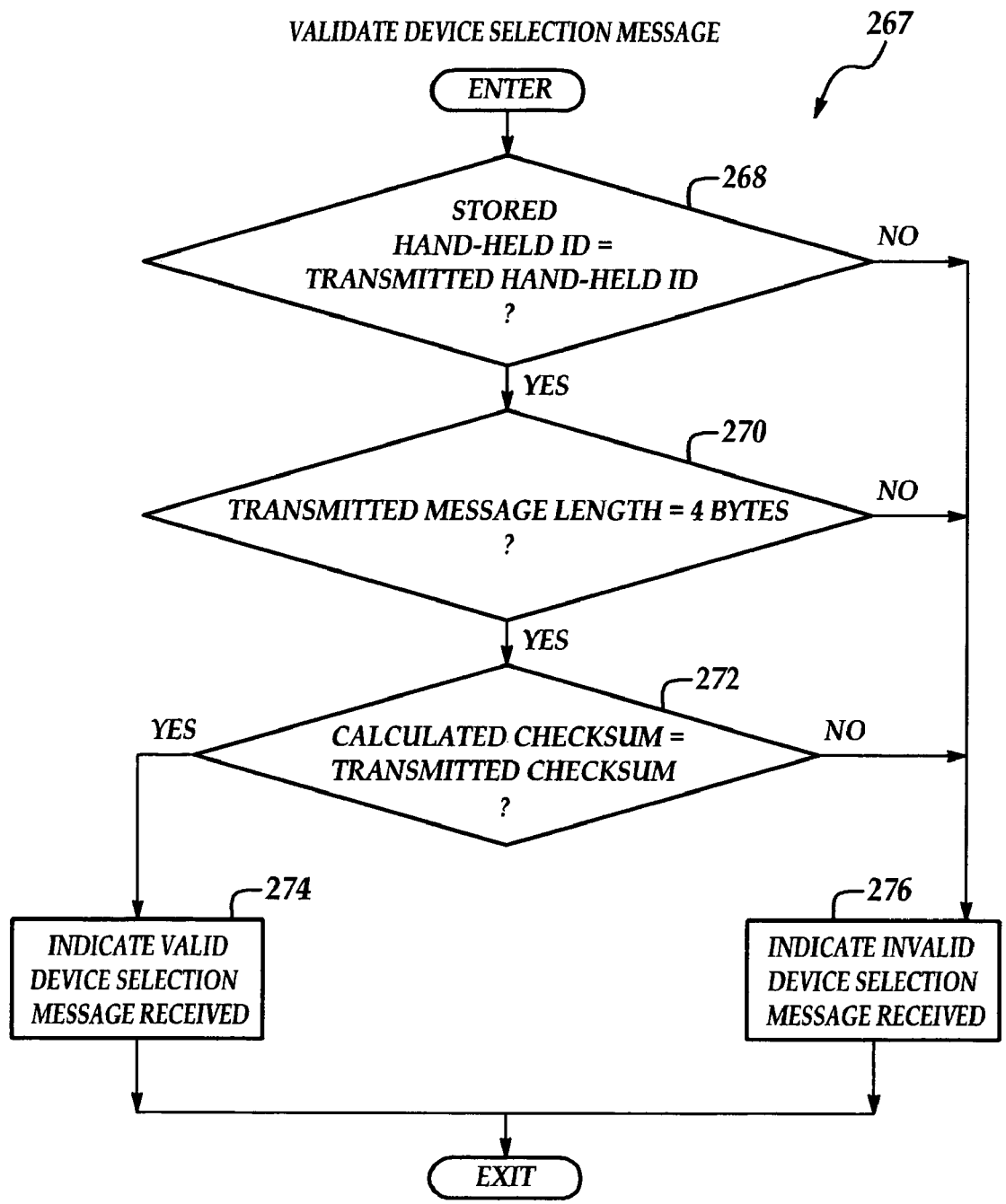

Referring to FIG. 12B, the method 267 for implementing step 258 for determining whether a valid "device selection message" was received by foot pedal control system 14 from handheld unit 12 will now be explained. At step 268, CPU 62 in foot pedal control system 14 makes a determination as to whether a Handheld ID stored in ROM 64 equals the Handheld ID contained in the "device selection message." If the value of step 268 equals "yes", the method advances to step 270. Otherwise, the method advances to step 276 that indicates an invalid "device selection message" was received by foot pedal control system 14.

At step 270, CPU 62 makes a determination as to whether the number of bytes of the transmitted "device selection message" equals the Message Length value contained in the "device selection message." If the value of step 270 equals "yes", the method advances to step 272. Otherwise, the method advances to step 276.

At step 272, CPU 62 makes a determination as to whether the checksum calculated from the received "device selection message" equals the Checksum value contained in the "device selection message." If the value of step 272 equals "yes", CPU 62 indicates that a valid "device selection message" was received. In particular, CPU 62 may set a internal memory flag equal to a logical "1" value. Otherwise, the method advances to step 276 where CPU 62 indicates that an invalid "device selection message" was received.

Figure 13A:
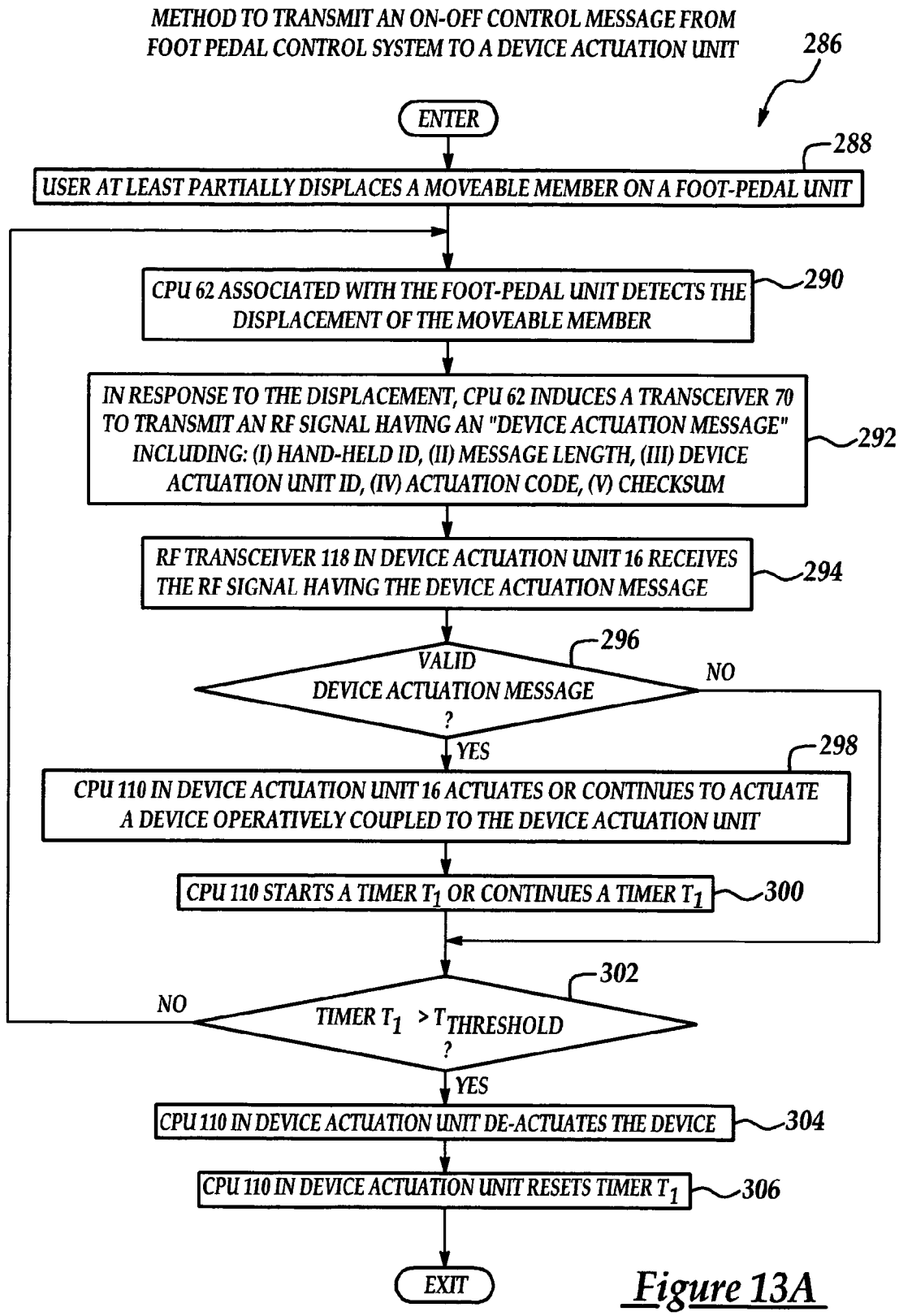
FIGS. 13A-13B are flowcharts of the method to transmit an "on-off" control message from a foot pedal control system to a device actuation unit.

Referring to FIG. 13A, a method 286 for transmitting a "device actuation message" from foot pedal control system 14 to device actuation unit 16 will now be explained.

At step 288, an operator's foot 87 at least partially displaces a movable member on foot pedal unit 84.

At step 290, CPU 62 detects the displacement of the movable member. It should be noted that several methods may be utilized to detect displacement of a movable member on a foot pedal unit. For example, referring to FIG. 3, CPU 62 may detect closure of a pneumatic switch (e.g. pneumatic switch 94) operably coupled to conduit 92 downstream of foot pedal unit 84. Closure of the pneumatic switch 94 would indicate that movable member 88 has been at least partially displaced by an operator.

Alternately, CPU 62 may received a signal (P) from a pressure sensor 94' operably coupled to conduit 92. When CPU 62 determines that the pressure signal indicates a pressure in conduit 92 greater than a predetermined pressure level, CPU 62 can determine that a movable member 88 has been at least partially displaced by an operator.

Alternately, referring to FIGS. 5 and 6, foot pedal unit 84 may be replaced with either a foot pedal unit 144 or a foot pedal unit 158. As shown, foot pedal unit 144 includes a housing 144, a movable member 150, and an electrical switch 146 operably coupled to movable member 150. Partial rotational displacement of movable member 150 closes electrical contact 146 which may be detected by CPU 62. Similarly, foot pedal unit 152 includes a housing 154, a movable member 156, and an electrical switch 158 operably coupled to movable member 156. Partial linear displacement of movable member 156 closes electrical switch 158 which may be detected by CPU 62.

Referring to again to FIG. 13A, at step 292, in response to displacement of the movable member, CPU 62 induces transceiver 70 to transmit an RF signal having a "device actuation message" including: (i) a Handheld ID, (ii) Message Length, (iii) Device Actuation Unit ID, (iv) Actuation Code, and (v) Checksum. The Checksum value may be determined by adding together the Device Actuation Unit ID and the Actuation Code. For example, transceiver 70 may transmit a "device selection message" 178.

At step 294, RF transceiver 118 in device actuation unit 16 receives the RF signal having the "device actuation message" from foot pedal control system 14.

At step 296, CPU 110 in device actuation unit 16 makes a determination as to whether the "device actuation message" is a valid message. If the value of step 296 equals "yes", the method advances to step 298. Otherwise, the method advances to step 302.

At step 298, CPU 110 in device actuation unit 16 actuates (e.g., turns on) or continues to actuate device 19 operably coupled to device actuation unit 16. In particular, CPU 110 can induce voltage driver 126 to close relay 132 to "turn on" or energize motor 140 of device 19.

At step 300, CPU 110 starts a timer TI or continues a timer T1.

At step 302, CPU determines whether the timer value associated with timer T1 is greater than a threshold time $T_{Threshold}$. If the value of step 302 equals "yes", the method advances to step 304. Otherwise, the method returns to step 290.

At step 304, CPU 110 induces voltage driver 126 to de-actuate device 19. In particular, CPU 110 can induce voltage driver 126 to open relay 132 to "turn off" or de-energize motor 140 of device 19. After step 306, method 286 is exited.

Figure 13B:
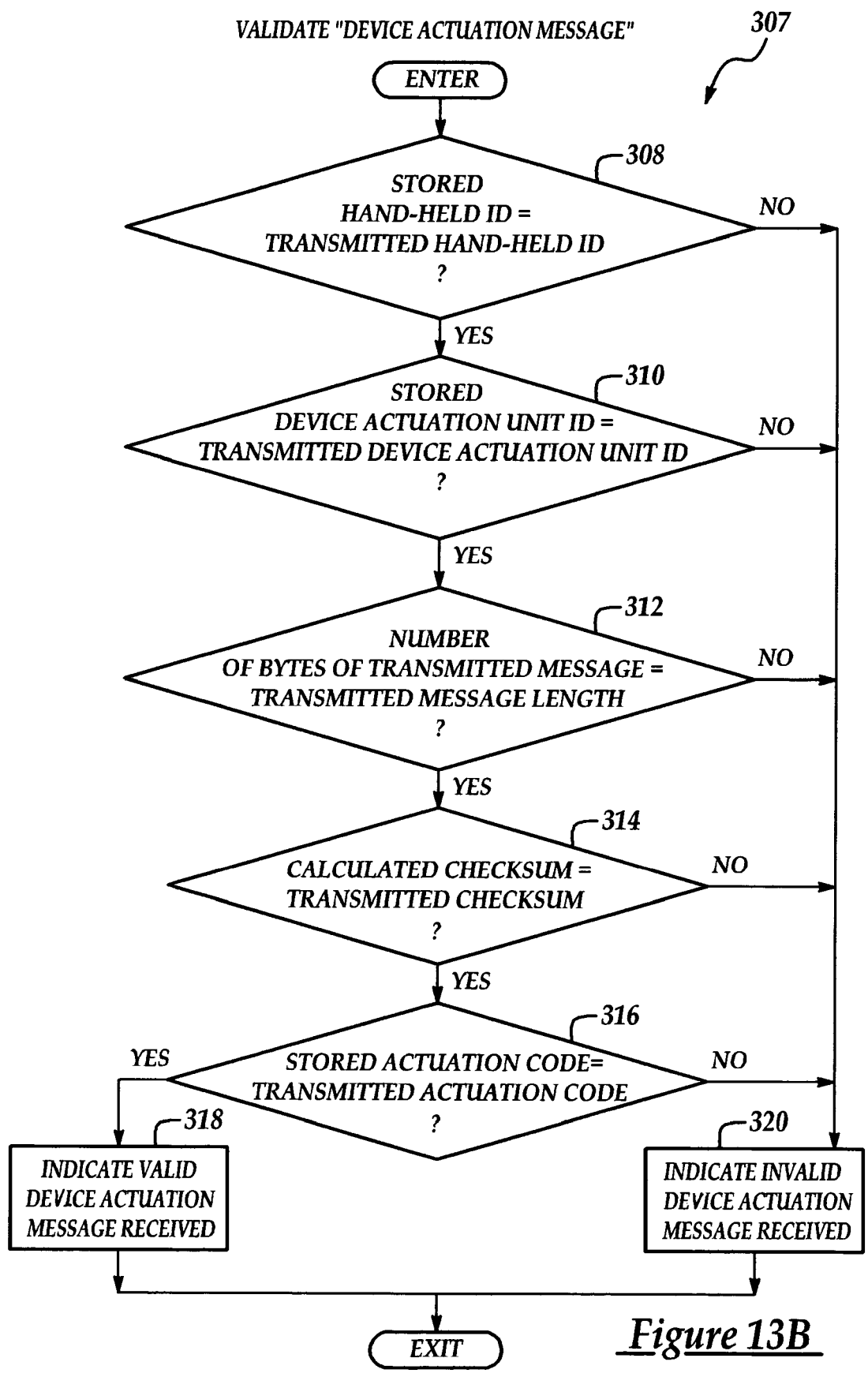

Referring to FIG. 13B, a method 307 for implementing step 296 for determining whether a valid "device actuation message" was received by device actuation unit 16 from foot pedal control system 14 will now be explained. At step 308, CPU 110 in device actuation unit 16 makes a determination as to whether a Handheld ID stored in ROM 112 equals the Handheld ID contained in the "device actuation message." If the value of step 308 equals "yes", the method advances to step 310. Otherwise, the method advances to step 320 that indicates an invalid "device selection message" was received by device actuation unit 16.

At step 310, CPU 110 makes a determination as to whether a Device Actuation Unit ID stored in ROM 112 equals the Device Actuation Unit ID contained in the "device actuation message". If the value of step 310 equals "yes", the method advances to step 312. Otherwise, the method advances to step 320.

At step 312, CPU 110 makes a determination as to whether the number of bytes of the transmitted "device actuation message" equals the Message Length value contained in the "device actuation message." If the value of step 312 equals "yes", the method advances to step 314. Otherwise, the method advances to step 320.

At step 314, CPU 110 makes a determination as to whether a checksum calculated from the received "device actuation message" equals the Checksum value contained in the "device actuation message." If the value of step 314 equals "yes", the method advances to step 316. Otherwise, the method advances to step 320.

At step 316, CPU 110 takes determination as to whether an actuation code stored in ROM 112 equals the Actuation Code contained in the "device actuation message." If the value of step equals "yes", CPU 110 indicates a valid "device actuation message" was received. In particular, CPU 110 may set an internal memory flag equal to a logical "1" value. Otherwise, the method advances to step 320 where CPU 110 indicates that an invalid "device actuation message" was received.

Figure 14:
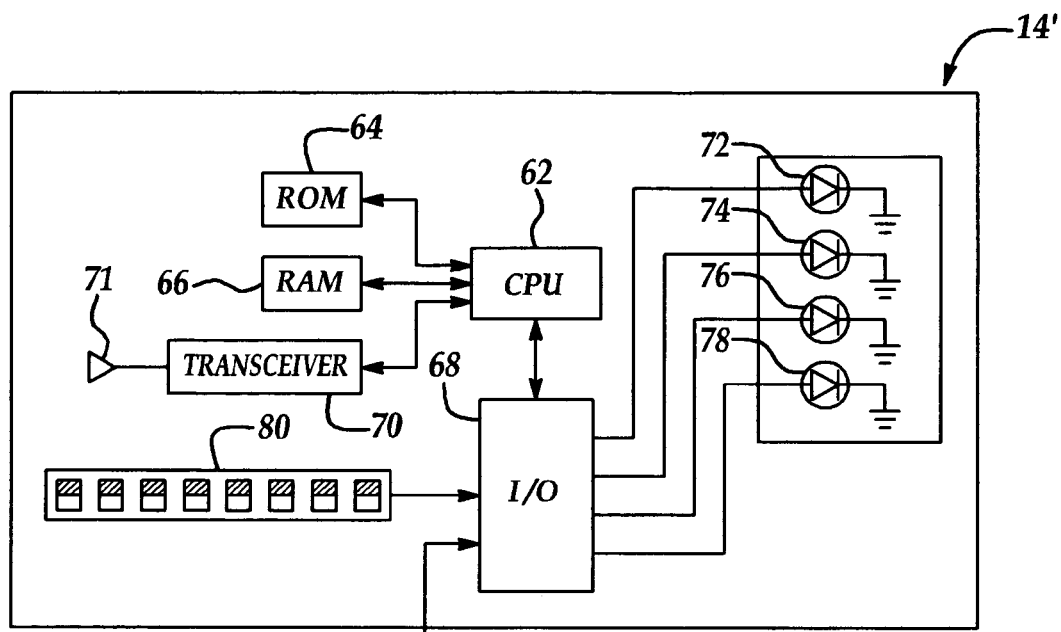
FIG. 14 is a schematic of a second embodiment of a foot pedal control system.

Referring to FIG. 14, a second exemplary embodiment of a foot pedal control system (e.g., foot pedal control system 14') is illustrated. The primary difference between foot pedal control systems 14 and 14', is that system 14 generates a "device actuation message" for "turning-on" or actuating a device, where system 14' generates a variable "device actuation message" for varying either (i) a speed of a device, such as a drill speed for example, (ii) a position of a member of the device, or (iii) an operational intensity of the device, such as an operational intensity of a laser for example.

Foot pedal control system 14' may include CPU 62', ROM 64, RAM 66, I/O interface 68, transceiver 70, antenna 71, LEDs 72, 74, 76, 78, a Handheld ID DIP switch 80, and a foot pedal unit 340.

Figure 15:
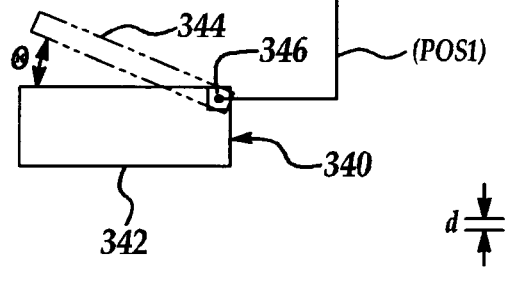
FIG. 15 is a schematic of a foot pedal unit that can generate a signal indicative of a position of a moveable member in the foot pedal unit.

Foot pedal unit 340 includes a housing 342, a movable member 344, and a position sensor 346 operably coupled to movable member 344. Position sensor 346 generates a signal (POSI) indicative of an angular position of movable member 344. CPU 62' may receive signal (POSI) and generate a variable "device actuation message" responsive thereto. In an alternate embodiment of foot pedal control system 14', foot pedal unit 340 could be replaced by foot pedal unit 348 (shown in FIG. 15) that includes a housing 350, a movable member 352, a position sensor 356, and a magnet 354. When depressed, movable member 352 can move linearly within housing 350. Movable member 352 may have a magnet 354 coupled thereto. Position sensor 356 may comprise a Hall Effect Sensor that detects the linear displacement (d) of magnet 354 and of movable member 352, and generates a signal (POS2) responsive thereto. CPU 62' may receive signal (POS2) and generate a variable "device actuation message" responsive thereto.

Referring to FIGS. 10 and 14, CPU 62' may generate a variable "device actuation message" having the following attributes: (i) Handheld ID, (ii) Message Length, (iii) Device Actuation Unit ID, (iv) a Variable Actuation Code, (v) a Command Code, (vi) Checksum. The Variable Actuation Code may be a unique number for instructing device actuation unit 16' that variable control of device 351 is desired. The Command Code corresponds to a computed variable value that can be utilized by device actuation unit 16' for varying the operational speed, operational position, or operational intensity of a device. In particular, the value of the Command Code may be increased as the angular displacement of movable member 344 (or the linear displacement of the member 352) from a non-depressed position increases. Similarly, the value of the Command Code may be decreased as the angular displacement of movable member 344 (or the linear displacement of the member 352) from a non-depressed position decreases. The Checksum value may be determined by adding together the Device Actuation Unit ID, the Variable Actuation Code, and the Command Code.

Figure 16:
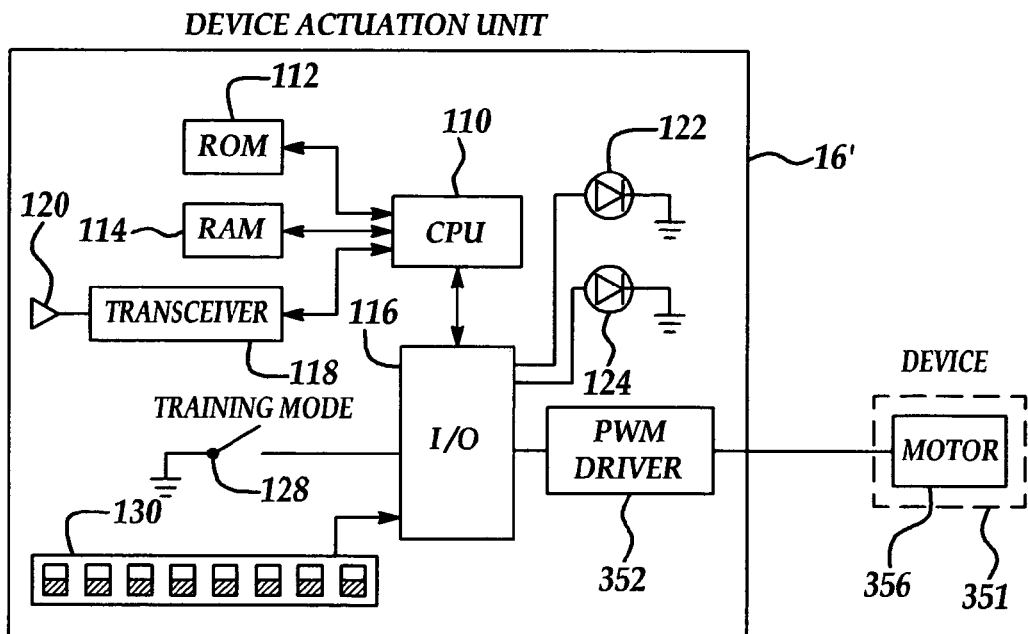
FIG. 16 is a schematic of a second embodiment of a device actuation unit.

Referring to FIG. 16, a second exemplary embodiment of a device actuation unit (e.g., device actuation unit 16') is illustrated. The primary difference between device actuation units 16 and 16' is that unit 16 "turns on" a device whereas unit 16 can variably control the operation of a device. For example, unit 16' can control the operational speed, operational position, or operational intensity of a device operably coupled to unit 16'.

As shown, device actuation unit 16' may include a pulse width modulation (PWM) driver 352 operably coupled to I/O interface 116. CPU 110' can induce PWM driver 352 to generate a PWM signal that can control the speed of a motor 356 of device 351 based upon a value of the Command Code in a received variable "device actuation message." It should be noted that device actuation unit 16' could be utilized to control any device which can be variably controlled. For example, device actuation unit 16' could be utilized to variably control: (i) a laser, (ii) a pneumatically or electrically actuated drill, (iii) a surgical microscope that can be automatically controlled, as discussed above, (iv) a microprocessor controlled anesthetic delivery system, as discussed above. It should be noted that PWM driver 352 could be replaced with any other type of known variable current driver or voltage driver for variably controlling a device. It should be further noted that PWM driver 352 (or an alternate variable current drive or voltage driver) could also be utilized to control a pneumatic valve (not shown) or a hydraulic valve (not shown) for further controlling operation of any pneumatically controlled device or hydraulically controlled device.

Figure 17:
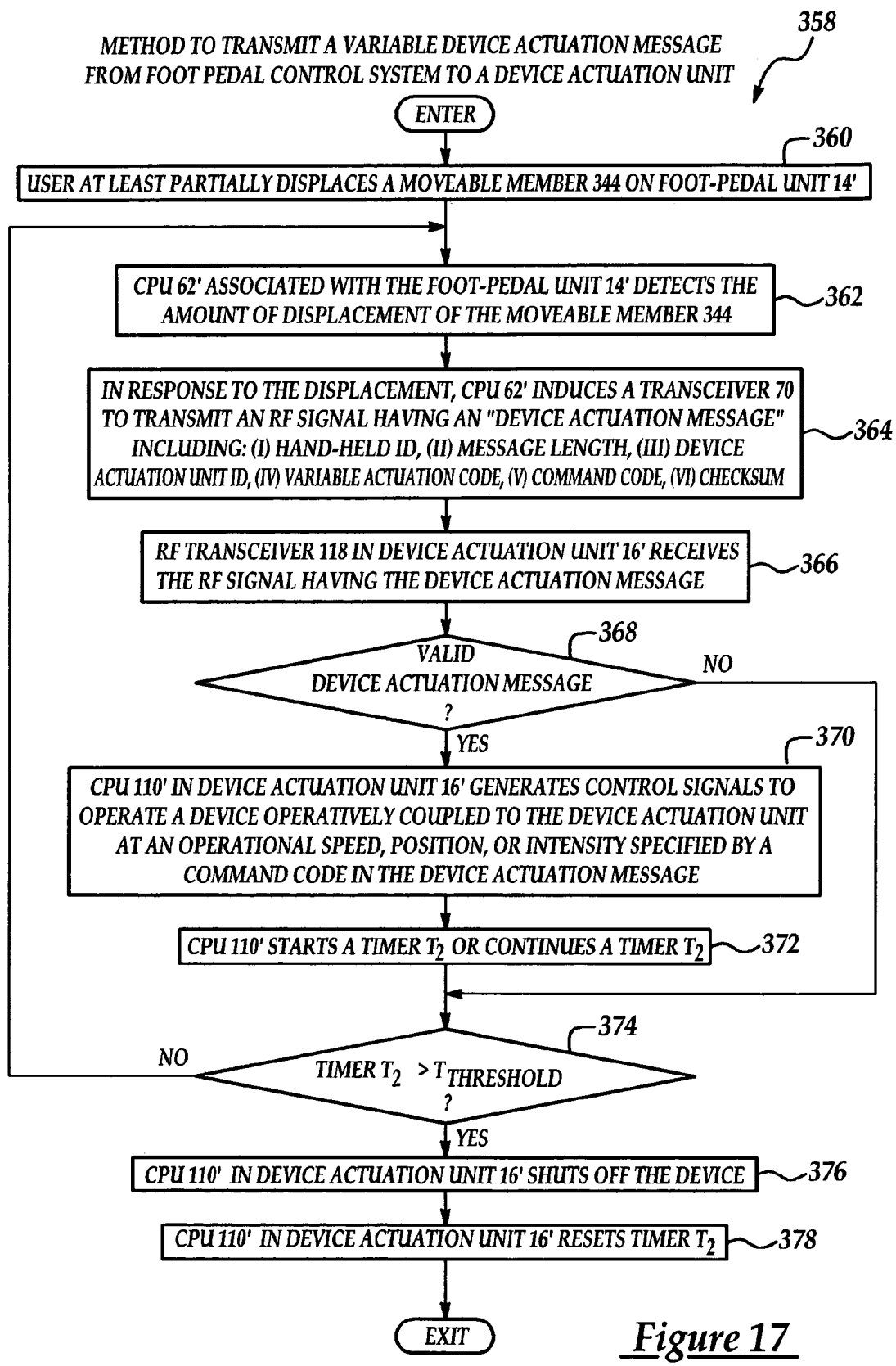
FIG. 17 is a flowchart of the method to transmit a variable-control control message from the foot pedal control system of FIG. 14 to the device actuation unit of FIG. 16.

Referring to FIG. 17, a method 358 for transmitting a variable "device actuation message" from foot pedal control system 14' to device actuation unit 16' will now be described.

At step 360, an operator of foot pedal control system 14' at least partially displaces the movable member 344 on foot pedal unit 340.

At step 362, CPU 62' determines an amount displacement of the movable member 344. As discussed above, CPU 62' may determine an amount of angular displacement of movable member 344, or alternately determine an amount of linear displacement of movable member 352.

At step 364, in response to displacement of movable member 344, CPU 62' induces transceiver 70 to transmit an RF signal having a variable "device actuation message" including: (i) a Handheld ID, (ii) Message Length, (iii) Device Actuation Unit ID, (iv) Variable Actuation Code, (v) Command Code, and (vi) Checksum. For example, transceiver 70 could transmit an RF signal having "device actuation message" 180.

At step 366, RF transceiver 118 in device actuation unit 16' receives the RF signal having the variable "device actuation message."

At step 368, CPU 110' in device actuation unit 16' makes a determination as to whether the variable "device actuation message" is a valid message. If the value of step 368 equals "yes", the method advances to step 370. Otherwise, the method advances to step 374.

At step 370, CPU 110' induces PWM driver 352 to generate PWM control signals to control operation of a device (e.g., device 20) coupled to unit 16' based on the Command Code in the variable "device actuation message." In particular, the PWM control signals can be utilized to control an operational speed, an operational position, or an operational intensity of a device.

At step 372, CPU 110' starts a timer T2 or continues a timer T2.

At step 374, CPU 110' determines whether the timer value associated with timer T2 is greater than a threshold time $T_{Threshold}$. If the value of step 374 equals "yes", the method advances to step 376. Otherwise, the method returns to step 362.

At step 376, CPU 110' induces PWM driver 352 to de-actuate or de-energize device 20.

At step 378, CPU 110' resets the timer T2. After step 378, the method 358 is exited.

Figure 18:
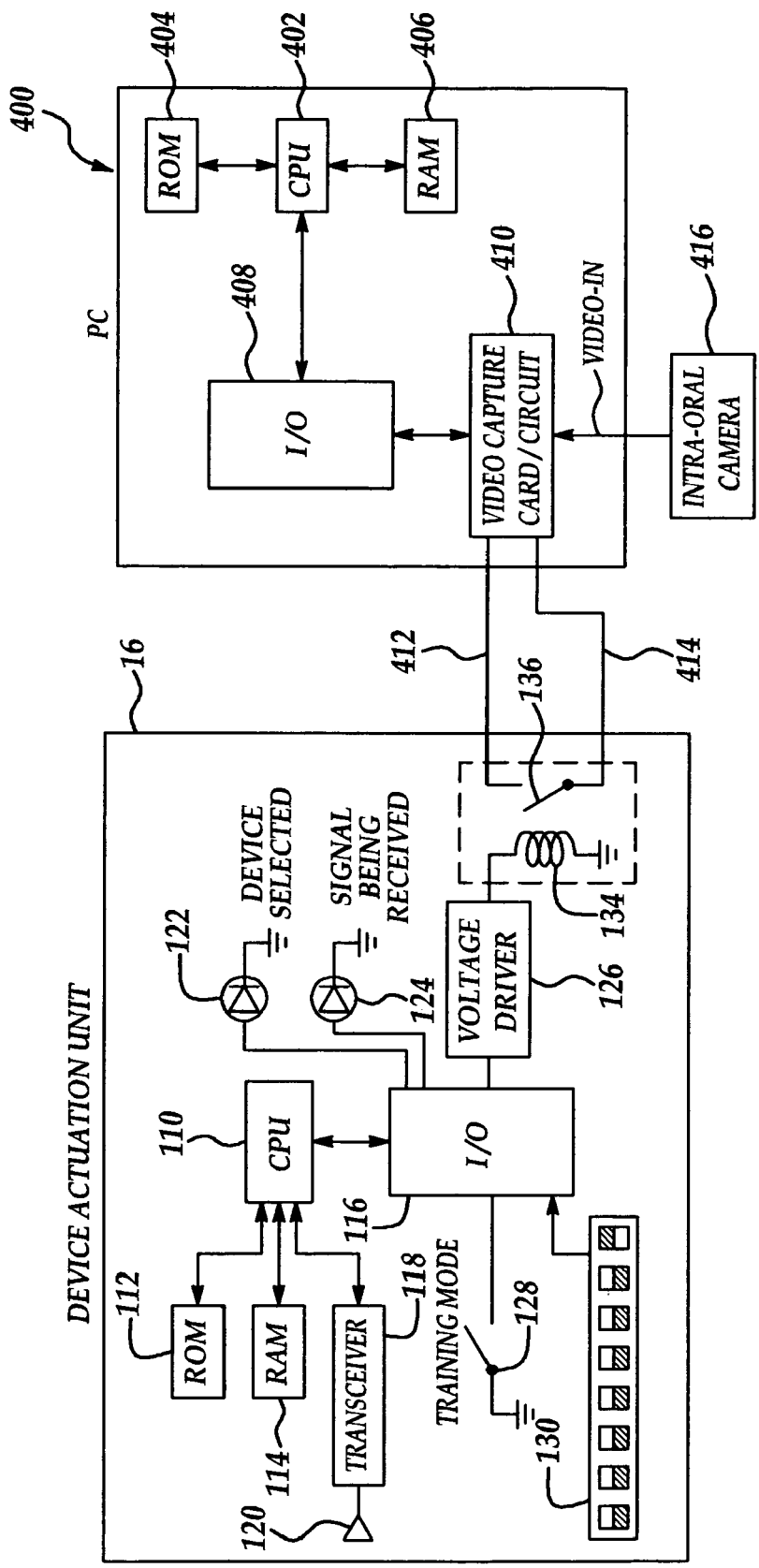
FIG. 18 is a schematic of a device actuation unit operably coupled to a video image capture system.

Referring to FIG. 18, a video image capture system 400 is illustrated that may be controlled by device actuation unit 16. Video image capture system 400 includes a CPU 402, a ROM 404, a RAM 406, an I/O interface 408, a video capture card/circuit 410, and an intra-oral camera 416.

Video capture card 410 is provided to generate, store, retrieve, display, or print a digital or analog video image from a (VIDEO-IN) signal received from an intra-oral camera 416. For example, video capture card 410 may comprise a video capture card sold under the trademark ADVC-50 A/D Converter, manufactured by Canopus Corporation of 711 Charcot Avenue, San Jose, Calif. 95131. Alternately, for example, video capture card 410 may comprise a video capture card sold under the trademark DVRaptor, manufactured by Canopus Corporation. Alternately, for example, video capture card 410 may comprise a video capture card sold under the trademark DVRaptor, manufactured by Canopus Corporation. Video capture card 410 may be induced to store a video image to a memory (not shown) when first and second electrical terminals (not shown) on card 410 coupled to electrical lines 412, 414, respectively, are electrically coupled together. Thereafter, video capture card 410 may transfer the digital or analog video image through I/O interface 408 to CPU 402 that may store the digital or analog video image in ROM 404 or RAM 406. CPU 402 may further display the digital or analog video image on a computer monitor (not shown) operably coupled to CPU 402.

Thus, when device actuation unit 16 receives a valid "device actuation message" from foot pedal control system 14, unit 16 can close contact 136. In response, video capture card 410 can store the image to an internal memory and also transfer the digital image to CPU 402. As discussed, CPU 402 can store the digital image in ROM 404 or RAM 406 and can display the image on a computer monitor.

The inventive system the method for remotely controlling devices provides a substantial advantage over other systems and methods. In particular, the system and method provide a foot pedal unit having one movable member that can be utilized to control multiple devices. Thus, an operator of the foot pedal unit can obtain a consistent control of multiple devices. Further, the single foot pedal unit can replace a plurality of other foot pedal units providing for a substantially less cluttered operatory floor.

What is claimed is:

1. A system for remotely controlling devices, comprising:
a foot pedal unit having a moveable member;
a first microprocessor operatively associated with the foot pedal unit and an RF transmitter, the first microprocessor configured to determine whether at least a first device or a second device is selected, the first microprocessor further configured to induce the RF transmitter to transmit a first RF signal in response to at least partial displacement of the moveable member when the first device is selected, the first RF signal having a first identifier value, the first microprocessor further configured to induce the RF transmitter to transmit a second signal in response to at least partial displacement of the moveable member when the second device is selected, the second RF signal having a second identifier value; and
a first device actuation unit configured to receive the first RF signal, the first device actuation unit further configured to compare the first identifier value to a first predetermined value associated with the first device, the first device actuation unit further configured to actuate the first device when the first identifier value corresponds to the first predetermined value.

2. The system of claim 1 wherein the first device actuation unit includes a second microprocessor and an RF receiver operably coupled to the second microprocessor.

3. The system of claim 1 further comprising a second device actuation unit configured to receive the second RF signal, the second device actuation unit further configured to compare the second identifier value to a second predetermined value associated with the second device, the second device actuation unit further configured to actuate the second device when the second identifier value corresponds to the second predetermined value.

4. The system of claim 1 further comprising an electrical switch operatively coupled to the moveable member and to the first microprocessor, wherein at least partial displacement of the moveable member actuates the electrical switch, the first microprocessor configured to induce the transmitter to transmit the first signal in response to actuation of the switch.

5. The system of claim 1 further comprising a pneumatic valve coupled to a conduit, the valve further operatively coupled to the moveable member, the system further including a pneumatic switch operatively coupled to the first microprocessor and to the conduit, wherein at least partial displacement of the moveable member actuates the pneumatic valve increasing a pressure in the conduit, when the pressure is greater than a predetermined pressure the pneumatic switch is actuated inducing the first microprocessor to induce the RF transmitter to transmit the first RF signal.

6. The system of claim 1 further comprising a pneumatic valve operatively coupled to a conduit, the valve being further operatively coupled to the movable member, the valve opening in response to at least partial displacement of the moveable member, the system further including a pressure sensor coupled to the conduit generating a pressure signal indicative of the pressure in the conduit that is transmitted to the first microprocessor.

7. The system of claim 6 wherein the first microprocessor is configured to induce the RF transmitter to generate the first RF signal when the pressure signal indicates the pressure is greater than a predetermined pressure.

8. The system of claim 6 wherein the first microprocessor is configured to induce the RF transmitter to generate the first RF signal containing a command value determined from the pressure signal.

9. The system of claim 1 further comprising a position sensor operatively coupled to the movable member of the foot pedal unit, the position sensor generating a third signal indicative of a position of the moveable member that is received by the first microprocessor, the first microprocessor configured to induce the RF transmitter to generate the first RF signal containing a command value determined from the position signal.

10. The system of claim 9 wherein the position signal is indicative of an angular position of the movable member.

11. The system of claim 9 wherein the position signal is indicative of a linear position of the movable member.

12. The system of claim 1 wherein the first device comprises a dental implement.

13. The system of claim 1 wherein the first device comprises a medical implement.

14. The system of claim 1 wherein the first device comprises one of a drill, a microprocessor position-controllable dental chair, an infrared photo-optic imaging camera, a dental irrigator, an intra-oral camera, a video capture circuit, a laser, an air-abrasion unit, an electro-surgery unit, an ultrasonic teeth cleaning unit, a piezo-ultrasonic unit, an air polishing prophylaxis device, a gum depth measurement probe, a surgical microscope with controllable focusing adjustment, a microprocessor controlled anesthetic delivery system, and an endodontic heat source device.

15. The system of claim 1 wherein the first device comprises a video capture board, the system further comprising a first device actuation unit operatively coupled to the video capture board, the first device actuation unit configured to receive the first RF signal and to induce the video capture board to store a video image in a memory in response to the first RF signal.

16. The system of claim 1 further comprising:
a second microprocessor operatively coupled to an RF receiver, and
an RF transmitter unit configured to transmit a third RF signal having the first predetermined value associated with the first device for selecting the first device, the second microprocessor being further configured to store the first predetermined value in a memory when the third RF signal is received by the RF receiver.

17. The system of claim 1 wherein the first microprocessor is further configured to induce the RF transmitter to transmit a third RF signal having the first identifier value in response to at least partial displacement of the moveable member when the first device is selected.

18. The system of claim 17 wherein the first device actuation unit is further configured to receive the third RF signal and to maintain activation of the first device during a first time period from at least receipt of the first RF signal to receipt of the third RF signal, if the first time period is less than or equal to a threshold time period.

19. A method for remotely controlling devices, comprising:
determining when a first device is selected, utilizing a microprocessor;
inducing an RF transmitter to transmit a first RF signal having a first identifier value in response to at least partial displacement of a moveable member on a foot pedal unit when the first device is selected, utilizing the microprocessor;
determining when a second device is selected, utilizing the microprocessor;
inducing the RF transmitter to transmit a second RF signal having a second identifier value in response to at least partial displacement of the moveable member on the foot pedal unit when the second device is selected, utilizing the microprocessor;
receiving the first RF signal at a device actuation unit;
comparing the first identifier value to a first predetermined value associated with the first device; and
controlling the first device utilizing the device actuation unit based on the first RF signal when the first identifier value corresponds to the first predetermined value associated with the first device.

20. The method of claim 19 further comprising controlling the second device utilizing the device actuation unit based on the second RF signal when the second identifier value corresponds to a second predetermined value associated with the second device.

21. The method of claim 19 wherein the first device comprises a dental implement or a medical implement.

22. The method of claim 19 wherein the first device comprises one of a drill, a microprocessor position-controllable dental chair, an infrared photo-optic imaging camera, a dental irrigator, an intra-oral camera, a video capture circuit, a laser, an air-abrasion unit, an electro-surgery unit, an ultrasonic teeth cleaning unit, a piezo-ultrasonic unit, an air polishing prophylaxis device, a gum depth measurement probe, a surgical microscope with controllable focusing adjustment, a microprocessor controlled anesthetic delivery system, and an endodontic heat source device.

23. The method of claim 19 wherein the controlling step includes inducing a video capture board to store a video image in a memory in response to the first signal.

24. The method of claim 19 further comprising:
inducing the RF transmitter to transmit a third RF signal having the first identifier value in response to at least partial displacement of the moveable member when the first device is selected; and
receiving the third RF signal at the device actuation unit and maintaining activation of the first device during a first time period from at least receipt of the first RF signal to receipt of the third RF signal, if the first time period is less than or equal to a threshold time period.

* * * * *